(12) United States Patent
Calhoun et al.

(10) Patent No.: US 10,898,212 B2
(45) Date of Patent: Jan. 26, 2021

(54) DEVICES AND METHODS FOR TREATING AN ARTERY

(71) Applicant: J.D. Franco & Co., Plano, TX (US)

(72) Inventors: Michael Calhoun, Lighthouse Point, FL (US); Robert Vidlund, Forest Lake, MN (US)

(73) Assignee: J.D. Franco & Co., LLC, Plano, TX (US)

( * ) Notice: Subject to any disclaimer, the term of this patent is extended or adjusted under 35 U.S.C. 154(b) by 169 days.

(21) Appl. No.: 15/993,359

(22) Filed: May 30, 2018

(65) Prior Publication Data

US 2018/0317944 A1 Nov. 8, 2018

Related U.S. Application Data

(63) Continuation-in-part of application No. PCT/US2018/031229, filed on May 4, 2018.
(Continued)

(51) Int. Cl.
*A61B 17/22* (2006.01)
*A61B 17/3207* (2006.01)
(Continued)

(52) U.S. Cl.
CPC ...... *A61B 17/22* (2013.01); *A61B 17/320783* (2013.01); *A61F 9/007* (2013.01);
(Continued)

(58) Field of Classification Search
CPC ........ A61B 17/12045; A61B 17/12109; A61B 17/12136; A61B 17/22;
(Continued)

(56) References Cited

U.S. PATENT DOCUMENTS 2,690,595 A 10/1954 Raiche
3,367,101 A 2/1968 Garnet et al.
(Continued)

FOREIGN PATENT DOCUMENTS

| WO | WO 98/52639 A1 | 11/1998 |
| WO | WO 98/53761 A1 | 12/1998 |

(Continued)

OTHER PUBLICATIONS

International Search Report and Written Opinion for International Application No. PCT/US2018/031229, dated Jul. 27, 2018 (19 pages).
(Continued)

*Primary Examiner* — Katherine M Shi
*Assistant Examiner* — Alyssa M Keane
(74) *Attorney, Agent, or Firm* — Bookoff McAndrews, PLLC

(57) ABSTRACT

A method for treating tissue of at least one of an internal carotid artery, an ophthalmic artery, or an ostium between the internal carotid artery and the ophthalmic artery of a subject may include expanding a first expandable device of a first device in the internal carotid artery. The method also may include delivering a second device in the ophthalmic artery via the first device and expanding a second expandable device of the second device in the ophthalmic artery. Further, the method may include adjusting a radial position of the second expandable device relative to the first expandable device.

20 Claims, 21 Drawing Sheets

Related U.S. Application Data

(60) Provisional application No. 62/523,724, filed on Jun. 22, 2017, provisional application No. 62/513,383, filed on May 31, 2017, provisional application No. 62/502,733, filed on May 7, 2017.

(51) Int. Cl.
*A61F 9/007* (2006.01)
*A61B 17/12* (2006.01)
*A61M 25/10* (2013.01)
*A61B 17/00* (2006.01)

(52) U.S. Cl.
CPC ... *A61B 17/12045* (2013.01); *A61B 17/12109* (2013.01); *A61B 17/12136* (2013.01); *A61B 2017/00358* (2013.01); *A61B 2017/12127* (2013.01); *A61B 2017/22001* (2013.01); *A61B 2017/22038* (2013.01); *A61B 2017/22039* (2013.01); *A61B 2017/22041* (2013.01); *A61B 2017/22048* (2013.01); *A61B 2017/22052* (2013.01); *A61B 2017/22054* (2013.01); *A61B 2017/22067* (2013.01); *A61B 2017/22069* (2013.01); *A61B 2017/22071* (2013.01); *A61B 2017/22079* (2013.01); *A61B 2017/22084* (2013.01); *A61M 2025/1015* (2013.01)

(58) Field of Classification Search
CPC .......... A61B 2017/00358; A61B 2017/12127; A61B 2017/22001; A61B 2017/22038; A61B 2017/22039; A61B 2017/22041; A61B 2017/22048; A61B 2017/22052; A61B 2017/22054; A61B 2017/22067; A61B 2017/22069; A61B 2017/22071; A61B 2017/22079; A61B 2017/22084; A61F 9/007; A61F 2/954; A61M 2025/1015; A61M 2025/1045
See application file for complete search history.

(56) References Cited

U.S. PATENT DOCUMENTS

| | | | |
|---|---|---|---|
| 3,435,826 A | 4/1969 | Fogarty | |
| 4,403,612 A | 9/1983 | Fogarty | |
| 4,795,433 A * | 1/1989 | Sarnoff | A61K 9/0019 604/134 |
| 4,926,858 A | 5/1990 | Gifford, III et al. | |
| 5,026,384 A | 6/1991 | Farr et al. | |
| 5,176,693 A | 1/1993 | Pannek, Jr. | |
| 5,395,311 A | 3/1995 | Andrews | |
| 5,415,634 A | 5/1995 | Glynn et al. | |
| 5,709,701 A | 1/1998 | Parodi | |
| 5,820,595 A | 10/1998 | Parodi | |
| 5,897,567 A | 4/1999 | Ressemann et al. | |
| 6,146,370 A | 11/2000 | Barbut | |
| 6,206,868 B1 | 3/2001 | Parodi | |
| 6,302,908 B1 | 10/2001 | Parodi | |
| 6,336,933 B1 | 1/2002 | Parodi | |
| 6,344,054 B1 | 2/2002 | Parodi | |
| 6,413,235 B1 | 7/2002 | Parodi | |
| 6,423,032 B2 | 7/2002 | Parodi | |
| 6,540,712 B1 | 4/2003 | Parodi et al. | |
| 6,623,471 B1 | 9/2003 | Barbut | |
| 6,641,573 B1 | 11/2003 | Parodi | |
| 6,645,222 B1 | 11/2003 | Parodi et al. | |
| 6,824,558 B2 | 11/2004 | Parodi | |
| 6,827,726 B2 | 12/2004 | Parodi | |
| 6,837,881 B1 | 1/2005 | Barbut | |
| 6,855,162 B2 | 2/2005 | Parodi | |
| 6,902,540 B2 | 6/2005 | Dorros et al. | |
| 6,905,490 B2 | 6/2005 | Parodi | |
| 6,908,474 B2 | 6/2005 | Hogendijk et al. | |
| 6,929,634 B2 | 8/2005 | Dorros et al. | |
| 6,936,053 B1 | 8/2005 | Weiss | |
| 6,936,060 B2 | 8/2005 | Hogendijk et al. | |
| 7,214,201 B2 | 5/2007 | Burmeister et al. | |
| 7,235,095 B2 | 6/2007 | Haverkost et al. | |
| 7,309,334 B2 | 12/2007 | Von Hoffmann | |
| 7,604,612 B2 | 10/2009 | Ressemann et al. | |
| 7,867,273 B2 | 1/2011 | Pappas et al. | |
| 7,901,445 B2 | 3/2011 | Walker et al. | |
| 7,927,347 B2 | 4/2011 | Hogendijk et al. | |
| 8,157,760 B2 | 4/2012 | Criado et al. | |
| 8,353,850 B2 | 1/2013 | Ressemann et al. | |
| 8,545,432 B2 | 10/2013 | Renati et al. | |
| 8,834,404 B2 | 9/2014 | Beaudin | |
| 8,852,226 B2 | 10/2014 | Gilson et al. | |
| 8,863,631 B1 | 10/2014 | Janardhan et al. | |
| 9,078,682 B2 | 7/2015 | Lenker et al. | |
| 9,241,699 B1 | 1/2016 | Kume et al. | |
| 9,259,215 B2 | 2/2016 | Chou et al. | |
| 9,265,512 B2 | 2/2016 | Garrison et al. | |
| 2001/0001114 A1 | 5/2001 | Tsugita et al. | |
| 2002/0087128 A1 | 7/2002 | Paques et al. | |
| 2002/0151922 A1 | 10/2002 | Hogendijk et al. | |
| 2003/0023200 A1 | 1/2003 | Barbut et al. | |
| 2003/0023227 A1 | 1/2003 | Zadno-Azizi et al. | |
| 2003/0199802 A1 | 10/2003 | Barbut | |
| 2003/0199819 A1 | 10/2003 | Beck | |
| 2003/0203958 A1 | 10/2003 | Kunz et al. | |
| 2005/0149117 A1 | 7/2005 | Khosravi et al. | |
| 2006/0089618 A1 | 4/2006 | McFerran et al. | |
| 2006/0136022 A1 | 6/2006 | Wong, Jr. et al. | |
| 2006/0259132 A1 | 11/2006 | Schaffer et al. | |
| 2008/0027519 A1 | 1/2008 | Guerrero | |
| 2008/0243229 A1 | 10/2008 | Wallace et al. | |
| 2009/0018455 A1 | 1/2009 | Chang | |
| 2009/0024072 A1 | 1/2009 | Criado et al. | |
| 2009/0030323 A1 | 1/2009 | Fawzi et al. | |
| 2010/0125244 A1 | 5/2010 | McAndrew | |
| 2011/0143993 A1 | 6/2011 | Langer et al. | |
| 2011/0152683 A1 | 6/2011 | Gerrans et al. | |
| 2011/0160762 A1 | 6/2011 | Hogendijk et al. | |
| 2012/0046679 A1 | 2/2012 | Patel et al. | |
| 2012/0078287 A1 | 3/2012 | Barbut | |
| 2012/0101510 A1 | 4/2012 | Lenker et al. | |
| 2013/0197621 A1 | 8/2013 | Ryan et al. | |
| 2013/0281788 A1 | 10/2013 | Garrison | |
| 2014/0154246 A1 | 6/2014 | Robinson et al. | |
| 2014/0243809 A1 * | 8/2014 | Gelfand | A61B 18/16 606/28 |
| 2015/0025562 A1 * | 1/2015 | Dinh | A61M 25/0009 606/191 |
| 2015/0032121 A1 | 1/2015 | Janardhan et al. | |
| 2015/0313607 A1 | 11/2015 | Zhadkevich | |
| 2015/0359547 A1 | 12/2015 | Vale et al. | |
| 2015/0366580 A1 | 12/2015 | Lenihan et al. | |
| 2016/0166754 A1 | 6/2016 | Kassab et al. | |
| 2016/0317328 A1 | 11/2016 | Berez et al. | |
| 2017/0239453 A1 | 8/2017 | Kawakita et al. | |
| 2017/0326001 A1 | 11/2017 | Franco et al. | |

FOREIGN PATENT DOCUMENTS

| | | |
|---|---|---|
| WO | WO 00/54673 A1 | 9/2000 |
| WO | WO 03/018085 A2 | 3/2003 |
| WO | WO 2007/103464 A2 | 9/2007 |
| WO | WO 2014/022866 A1 | 2/2014 |
| WO | WO 2016/109586 A1 | 7/2016 |
| WO | WO 2017/156333 A1 | 9/2017 |
| WO | WO 2018/053121 A1 | 3/2018 |
| WO | WO 2018/106858 A1 | 6/2018 |

OTHER PUBLICATIONS

Altinbas, N.K. et al, "Effect of Carotid Artery Stenting on Ophthalmic Artery Flow Patterns," Journal of Ultrasound Medicine, 2014; 33: pp. 629-638.

(56) References Cited

OTHER PUBLICATIONS

Ambarki, K. et al., "Blood Flow of Ophthalmic Artery in Healthy Individuals Determined by Phase-Contrast Magnetic Resonance Imaging," Investigative Ophthalmology & Visual Science, 2013; 54: pp. 2738-2745.

Hayreh, S.S., "The Ophthalmic Artery III. Branches," British Journal of Ophthalmology, 1962, 46, pp. 212-247.

Hwang, G. et al., "Reversal of Ischemic Retinopathy Following Balloon Angioplasty of a Stenotic Ophthalmic Artery." Journal of Neuro-Ophthalmology 30.3, 2010, pp. 228-230.

Kane, A.G. et al., "Reduced Caliber of the Internal Carotid Artery: A Normal Finding with Ipsilateral Absence or Hypoplasia of the A1 Segment," American Journal of Neuroradiology, 1996; 17: pp. 1295-1301.

Kawa, M.P. et al., "Complement System in Pathogenesis of AMD: Dual Player in Degeneration and Protection of Retinal Tissue," Hindawi Publishing Corporation, Journal of Immunology Research, vol. 2014, Article ID 483960, 12 pages.

Klein, R. et al., "Vasodilators, Blood Pressure-Lowering Medications, and Age-Related Macular Degeneration," American Academy of Ophthalmology, 2014, vol. 121, Issue 8, pp. 1604-1611.

Kooragayala, K. et al., "Quanitification of Oxygen Consumption in Retina Ex Vivo Demonstrates Limited Reserve Capacity of Photoreceptor Mitochondria," Investigative Ophthalmology & Visual Science, 2015; 56: pp. 8428-8436.

Krejza, J. et al., "Carotid Artery Diameter in Men and Women and the Relation to Body and Neck Size," Stroke, 2006; 3 pages.

Lanzino, G. et al., "Treatment of Carotid Artery Stenosis: Medical Therapy, Surgery, or Stenting?," Mayo Clinic Proceedings, Apr. 2009; 84(4), pp. 362-368.

Michalinos, A. et al., "Anatomy of the Ophthalmic Artery: A Review concerning Its Modern Surgical and Clinical Applications," Hindawi Publishing Corporation, Anatomy Research International, vol. 2015, Article ID 591961, 8 pages.

Paques, M. et al., "Superselective ophthalmic artery fibrinolytic therapy for the treatment of central retinal vein occlusion." British Journal of Ophthalmology, 2000, 85: 1387-1391.

Tan, P.L. et al., "AMD and the alternative complement pathway: genetics and functional implications," Human Genomics, 2016, 10:23, 13 pages.

Xu, H. et al., "Targeting the complement system for the management of retinal inflammatory and degenerative diseases," European Journal of Pharmacology, 2016, 787, pp. 94-104.

Yamane, T. et al., "The technique of ophthalmic arterial infusion therapy for patients with intraocular retinoblastoma," International Journal of Clinical Oncology, Apr. 2004; vol. 9, Issue 2, pp. 69-73.

Zeumer, H. et al., "Local intra-arterial fibrinolytic therapy in patients with stroke: urokinase versus recombinant tissue plagminogen activator (r-TPA)," Neuroradiology, 1993; 35: pp. 159-162.

Zipfel, P.F., et al., "The Role of Complement in AMD," Inflammation and Retinal Disease: Complement Biology and Pathology, Advances in Experimental Medicine and Biology, 2010, 703, pp. 9-24.

Examination Report No. 2 for AU Application No. 2013296195, dated Jun. 27, 2017 (6 pages).

Notice of Allowance for KR 20157005602, dated Sep. 25, 2017 (3 pages).

Loh, K. et al., "Prevention and management of vision loss relating to facial filler injections." Singapore Medical Journal, 2016; 57(8): 438-443.

International Search Report and Written Opinion for International Application No. PCT/US2017/051551, dated Dec. 15, 2017 (14 pages).

International Search Report and Written Opinion for International Application No. PCT/US2017/052901, dated Dec. 8, 2017 (9 pages).

* cited by examiner

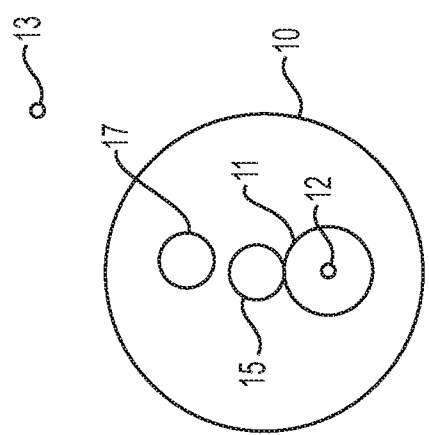
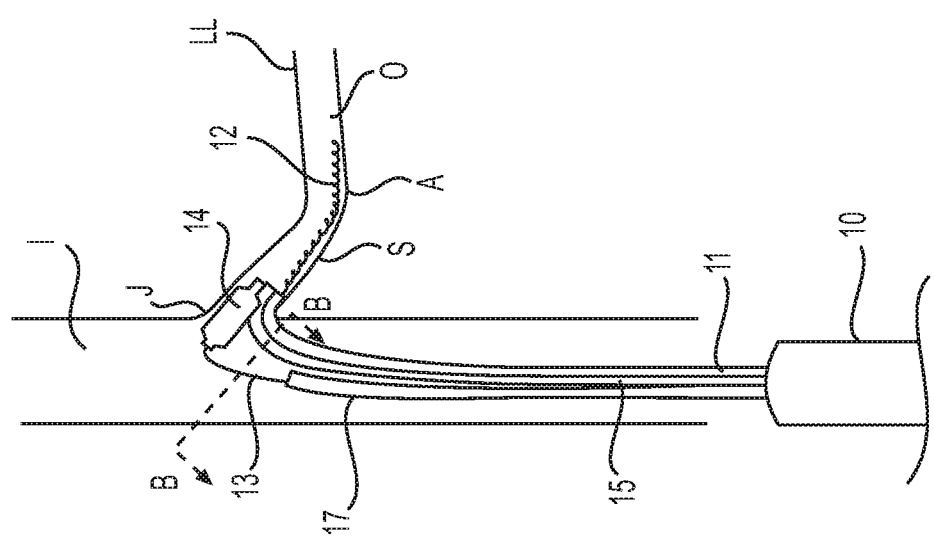
FIG. 1B
FIG. 1A

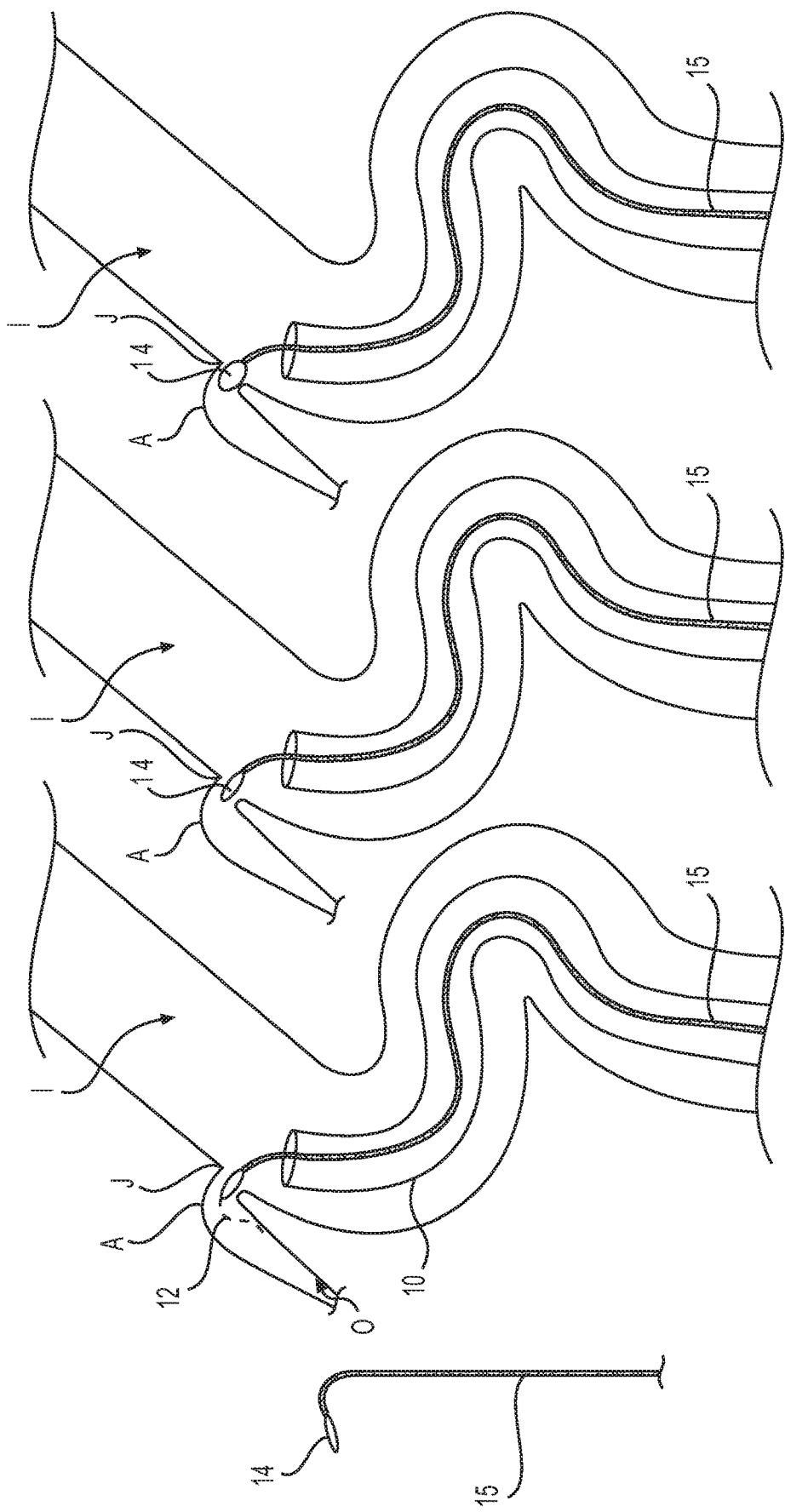

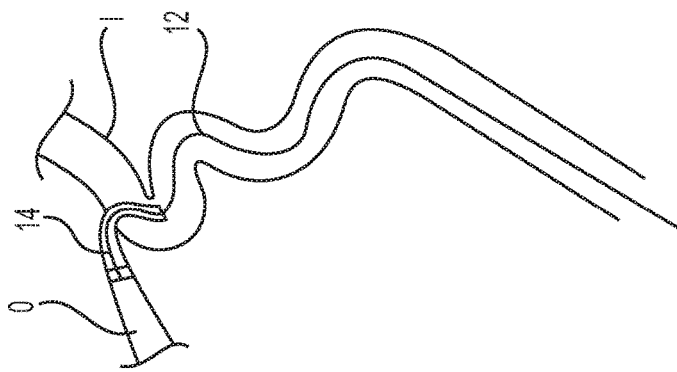
FIG. 12D
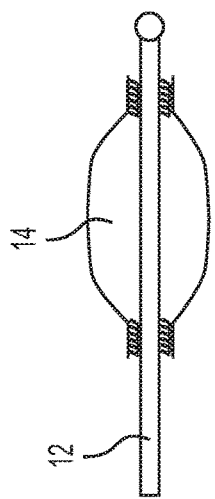
FIG. 12A
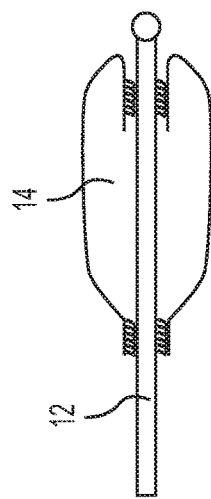
FIG. 12B
FIG. 12C

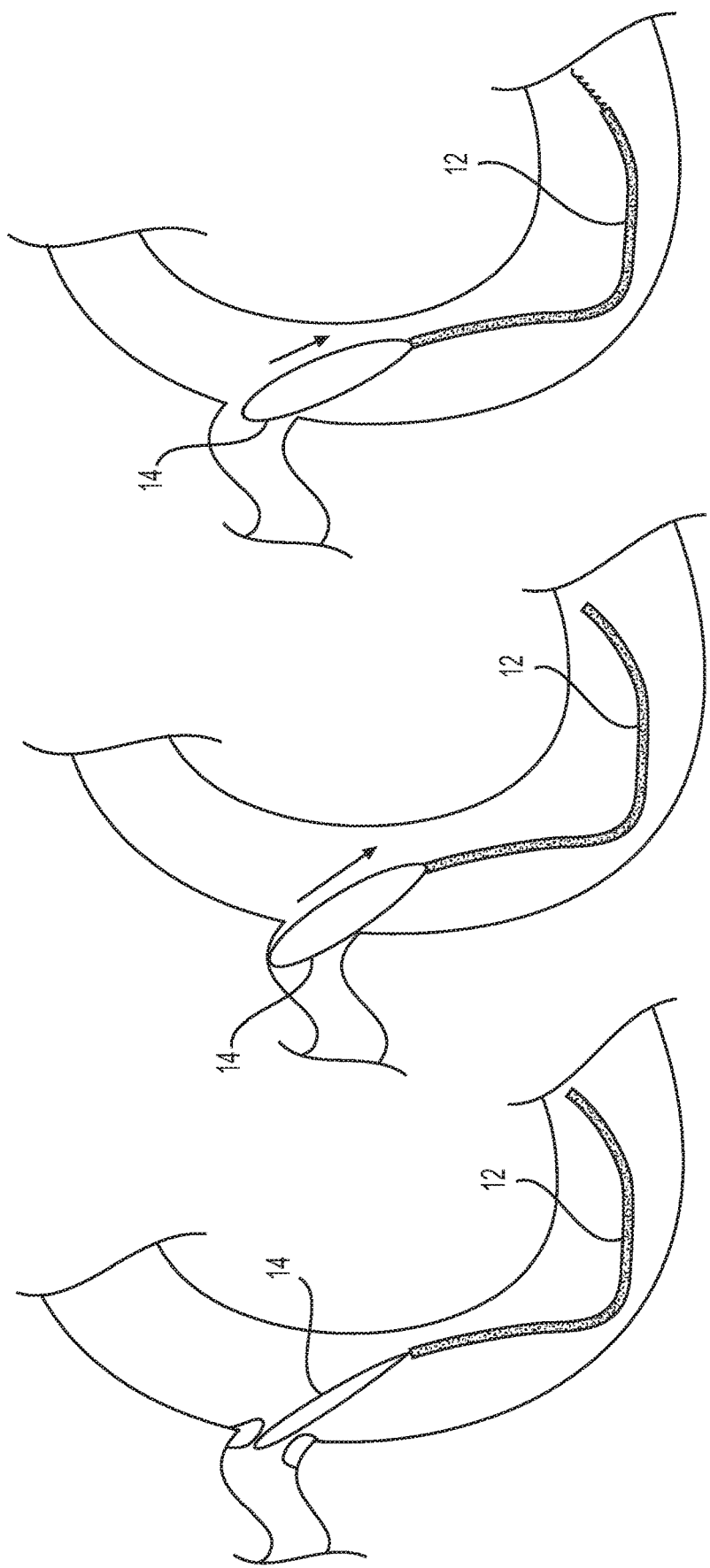

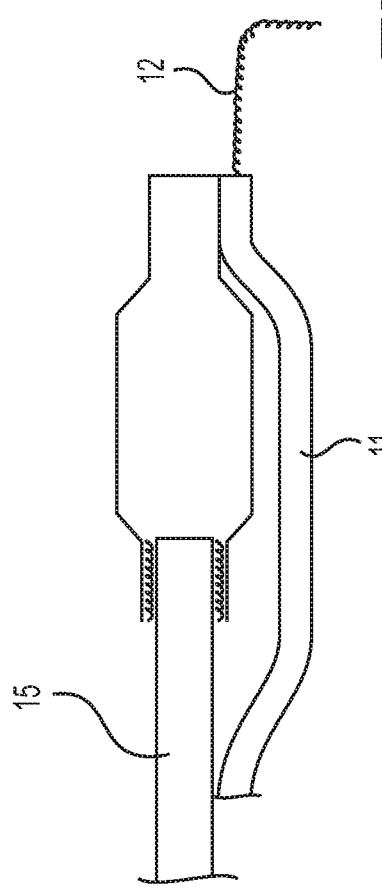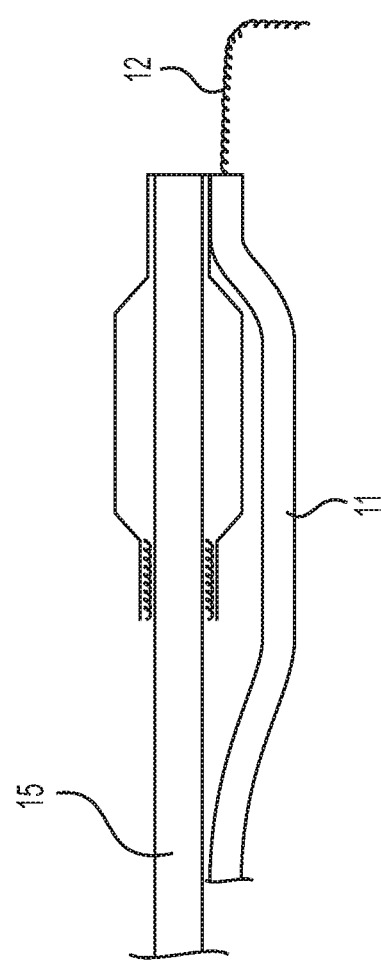

A
DEVICES AND METHODS FOR TREATING AN ARTERY

I. CROSS-REFERENCES TO RELATED APPLICATIONS

This application is a continuation-in-part application of International Application No. PCT/US2018/031229, filed on May 4, 2018, and claims the benefit under 35 U.S.C § 119(e) of U.S. Provisional Application No. 62/502,733, filed May 7, 2017, U.S. Provisional Application No. 62/513,383, filed May 31, 2017, and U.S. Provisional Application No. 62/523,724, filed Jun. 22, 2017, the entirety of each of which is incorporated by reference herein.

II. FIELD

The present disclosure relates to medical devices, systems and related methods for removal and/or treatment of one or more of a blockage, lesion, or other tissue in a small diameter artery, such as the ophthalmic artery. Additionally, the present disclosure relates to medical devices, systems, and related methods of improving or restoring blood flow in such an artery, and/or to treating an eye disease or condition.

III. BACKGROUND

Diseases of the eye, specifically age-related macular degeneration (AMD), glaucoma, and diabetic retinopathy affect a large percentage of the population. In part, most of the diseases of the eye are treated by treating one or more symptoms, but failing to address the underlying cause(s) of the disease or condition. These therapies are therefore deficient in one or more aspects, necessitating improved approaches.

In a general sense, the pathogenesis of some eye diseases is similar if not the same as those seen for cardiac diseases and for abdominal aorta conditions. However, the anatomy of the vasculature behind the eye is typically smaller, includes more branches, and includes more sharp angles in the blood flow pathway. Further, the vascular system supplying blood to the eye is closer to the brain and any uncaptured or non-rerouted debris may, upon reaching the brain, cause an immediate stroke.

The use of catheter delivery systems for positioning and deploying therapeutic devices, such as balloons, stents and embolic devices, in the vasculature of the human body has become a standard procedure for treating endovascular diseases. It has been found that such devices are particularly useful as an alternative in treating areas where traditional operational procedures are impossible or pose a great risk to the patient. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

Obstructive emboli have also been mechanically removed from various sites in the vasculature for years. For example, an embolectomy catheter such as, for example, a "Fogarty catheter," or variations thereof, has been used to remove clots from arteries found in legs and in arms. These well-known devices are described, for example, in U.S. Pat. No. 3,435,826 to Fogarty, and in U.S. Pat. Nos. 4,403,612 and 3,367,101. In general, these patents describe a balloon catheter in which a balloon material is longitudinally stretched when deflated.

In procedures for removing emboli using such embolectomy catheters or other similar catheters, it is typical to first locate the clot using fluoroscopy. Next, the embolectomy catheter is inserted and directed to the clot. The distal tip of the catheter is then carefully moved through the center of the clot. Once the balloon has passed through the distal side of the clot, the balloon is inflated. The catheter is then gradually, proximally withdrawn. The balloon, in this way, acts to pull the clot proximally ahead of the balloon to a point where it can be retrieved. The majority of procedures using a Fogarty-type catheter repeat these steps until the treated vessel is cleared of clot material.

A variety of alternative emboli retrieval catheters have also been developed, in which various wire corkscrews and baskets must be advanced distally through the embolic material in order to achieve capture and removal. However, removal of emboli using such catheters may give rise to potential problems. One such problem may occur when advancing the catheter through the clot dislodges material to a more remote site where removal may become more difficult or impossible.

The terms proximal and distal, as used herein, refer to a direction or a position along a longitudinal axis of a catheter or medical instrument. Proximal refers to the end of the catheter or medical instrument closer to the operator, while distal refers to the end of the catheter or medical instrument closer to the patient.

The measurement term French, abbreviated Fr or F, is defined as three times the diameter of a device as measured in mm. Thus, a 3 mm diameter catheter is 9 French in diameter.

There are various terms for the parts of the anatomy from the internal carotid artery (ICA) through the ophthalmic artery (OA) to the eye. Hayreh et al. (*Brit. J. Ophthal.*, 46, 65 (1962)), incorporated by reference in its entirety herein, particularly FIG. 4, illustrates the ICA and the OA. Specifically, the OA branches off the ICA in a portion called the "short limb." An "angle a" is a distinctive turn in the OA near an end of the short limb, and the "long limb" is the portion of the OA before it penetrates into the dural sheath. One skilled in the art will readily recognize that while these are typical or common structures, not all subjects/patients/humans have these exact same structures, e.g., there are human population variations.

IV. SUMMARY

The present disclosure is directed to one or more intravascular medical devices and methods intended to sufficiently unblock or at least partially restore blood flow in a blocked or partially blocked artery such that nutrient(s) content is increased distal to the blockage. An embodiment of the present disclosure is directed to devices and methods for restoring blood flow through the ostium between an internal carotid artery (ICA) and an ophthalmic artery (OA) of a subject. An embodiment of the present disclosure includes using these devices and methods to restore or increase blood flow to the eye or a portion thereof. An embodiment of the present disclosure includes restoring or increasing nutrient levels in the eye or a portion thereof. Restoring or increasing blood flow may include using these devices and methods, or equivalent devices and methods, but is not to be limited thereby.

As used herein, blockage, occlusion, or obstruction refers to complete or partial blockage resulting in reduced, restricted, or eliminated blood flow and is sometimes caused by plaque or other tissue, tortuous shaped anatomy, vessel failure and/or dysfunction.

The Circle of Willis, as used herein, refers to interconnected cranial arteries between branches of the internal carotid arteries and the vertebral arteries at the base of the brain.

Superior (or cranial), as used herein, refers to a location above a horizontal plane extending through an identified anatomical structure. Inferior (or caudal), as used herein, refers to a location below a horizontal plane extending through an identified anatomical structure. For example, at least a portion of the Circle of Willis is superior to the ophthalmic artery.

While not intending to be restricted to any particular theory of operation, function, or causal connection, it is believed that a condition, such as a blockage, that leads to lowered nutrient availability and/or consumption contributes to abnormal physiologic function. Also, it is believed that those conditions may reduce metabolic waste removal from cells, organs, and other biological structures.

Possible such conditions include but are not limited to one or more of the following: reduced or blocked blood flow in one or more arteries or system of arteries; reduced or blocked source of energy or nutrients to a cell, organelle of a cell, mitochondrion, group of cells, or organ; altered aerobic energy metabolism; altered mitochondria oxidative phosphorylation; decreased or blocked supply of glucose; decreased hemoglobin amount or delivery to one or more intra-cranial structures or to one or more eye tissues; reduced blood flow or rate anywhere in the fluid flow path between the ICA and eye tissue; blockage or partial blockage in one or more arteries or system of arteries; any compromise of the complement system, the complement cascade, and/or one of the complement cascade associated molecules; and lowered/blocked nutrient supply and/or metabolic waste removal.

These conditions may occur in one or more of the following areas or structures: one or more arteries; one or more cranial arteries; and one or more arteries associated with of supplying blood flow to the eye; the ICA; the OA; anywhere in the fluid flow path between the ICA and eye tissue; the junction between the ICA and the OA, which is referred to in this disclosure as the ostium; and secondary areas of the anatomy including the vascular system (commonly referred to as the terminal branches). These secondary areas include, but are not limited to the supra orbital artery (SOA), the supra trochlear artery (STA), the dorsal nasal artery (DNA), and the facial arteries (FA); any cranial artery; and in any of the junctions or ostia between any of the vasculature between the ICA and one or more eye tissues.

Examples of diseases and conditions that can occur in these blood vessels, and which may be treated by systems and methods described herein, may include, but are not limited to, any of a variety of eye diseases, including but not limited to AMD (both dry and wet); neuronal cell death; Alzheimer's disease; dementia; glaucoma; diabetic macula edema, macular telangiectasia (e.g., type 1 or 2 macular telangiectasia), atrophic macular degeneration, chorioretinopathy (e.g., central serous chorioretinopathy), retinal inflammatory vasculopathy, pathological retinal angiogenesis, age-related maculopathy, retinoblastoma, pseudoxanthoma elasticum, vitreoretinal disease, choroidal sub-retinal neovascularization, central serous chorioretinopathy, ischemic retinopathy, hypertensive retinopathy or diabetic retinopathy (e.g., nonproliferative or proliferative diabetic retinopathy, such as macular edema or macular ischemia), retinopathy of prematurity (e.g., associated with abnormal growth of blood vessels in the vascular bed supporting the developing retina), venous occlusive disease (e.g., a retinal vein occlusion, branch retinal vein occlusion or central retinal vein occlusion), arterial occlusive disease (e.g., branch retinal artery occlusion (BRAO), central retinal artery occlusion or ocular ischemic syndrome), central serous chorioretinopathy (CSC), cystoid macular edema (CME) (e.g., affecting the central retina or macula, or after cataract surgery), retinal telangiectasia (e.g., characterized by dilation and tortuosity of retinal vessels and formation of multiple aneurysms, idiopathic JXT, Leber's miliary aneurysms, or Coats' disease), arterial macroaneurysm, retinal angiomatosis, radiation-induced retinopathy (RIRP), or rubeosis iridis (e.g., associated with the formation of neovascular glaucoma, diabetic retinopathy, central retinal vein occlusion, ocular ischemic syndrome, or chronic retinal detachment); distortions and/or blind spots (scotoma); changes in dark adaptation (diagnostic of rod cell health); changes in color interpretation (diagnostic of cone cell health); decrease in visual acuity; and cataract (e.g., age-related cataract).

Methods and devices are also described in this disclosure for OA interventional procedures, such as stenting, angioplasty, and atherectomy, performed through a transcervical or transfemoral approach into the OA, either using an open surgical technique or using a percutaneous technique, such as a modified Seldinger technique. Some of these methods and devices are particularly useful in procedures which use reverse or retrograde flow protocols (e.g., such as those that impede, block, or otherwise stop antegrade blood flow).

The disclosed methods and devices include arterial access sheaths, closure devices, and/or interventional catheters. The methods and devices described herein are useful for procedures utilizing any method of embolic protection, including distal filters, flow occlusion, retrograde flow, or combinations of these methods, or for procedures which do not use any method of embolic protection. Specific methods and devices for embolic protection are also described.

The present disclosure provides a system useable for performing a therapeutic and/or diagnostic task at a location within the body of a human or animal subject. Such a system may include a catheter that has a proximal portion, a distal portion, a lumen and a distal end opening. The catheter may be transitionable from a first configuration in which the distal portion has a first outer diameter that is smaller than an outer diameter of the proximal portion, and a second configuration in which the distal portion is expanded to a second outer diameter that is larger than the first outer diameter and, in some embodiments, no larger than the outer diameter of the proximal portion. The described system may further include a working device that can be advanced though the lumen of the catheter and out of the distal opening of the catheter at least when the distal portion of the catheter is in is second configuration. The working device may be useable to perform a therapeutic or diagnostic task. Examples of the types of working devices that may be used in this system include, but are but are not limited to, (i) devices for removing thrombus or other obstructive matter from body lumens, (ii) flow restoration devices useable to facilitate flow of a fluid though or around an obstruction within a body lumen, and (iii) devices for deploying or delivering implants (e.g., implantable occlusion coils or implantable embolic devices).

Further in accordance with the present disclosure, there is provided a method for performing a therapeutic or diagnostic task at a location within the body of a human or animal subject. Such a method may include inserting into the subject's body a catheter that has a proximal portion, a distal portion, a lumen, and a distal end opening. The catheter may be transitionable from a first configuration in which the distal portion has a first outer diameter that is smaller than an outer diameter of the proximal portion and a second configuration in which the distal portion is expanded to a second outer diameter that is larger than the first outer diameter and, in some embodiments, no larger than the outer diameter of the proximal portion. The method may further include positioning the distal end opening of the catheter in a desired body lumen while the distal portion of the catheter is in its first configuration. Further, the method may include causing the distal portion of the catheter to transition to the second configuration, advancing a working device though the lumen of the catheter and out of the distal opening, and using the working device to perform the therapeutic or diagnostic task. Examples of the types of working devices that may be used in this method include, but are but are not limited to, devices for removing thrombus or other obstructive matter from body lumens, flow restoration devices useable to restore blood flow through an obstructed body lumen, and devices for delivering implants (e.g., implantable occlusion coils or embolic devices).

In a further aspect, there is provided a method for removing obstructive matter from a body lumen. Such a method may include inserting a catheter that has a proximal portion, a distal portion, a lumen and a distal end opening into the body of a subject. The catheter may be transitionable from a first configuration in which the distal portion has a first outer diameter that is smaller than an outer diameter of the proximal portion and a second configuration in which the distal portion is expanded to a second outer diameter that is larger than the first outer diameter and, in some embodiments, no larger than the outer diameter of the proximal portion. The method may further include positioning the catheter, while in the first configuration, such that its distal end opening of the catheter is within a body lumen of the subject, causing the catheter to transition from the first configuration to the second configuration, moving obstructive matter through the distal end opening and into the lumen of the catheter, and removing the catheter along with the obstructive matter that has been moved into the lumen of the catheter. In some embodiments, negative pressure may be applied through the lumen of the catheter to aspirate obstructive matter through the distal end opening and into the lumen of the catheter.

In some embodiments, advancing a working device through a lumen of the catheter or moving obstructive matter through the distal opening of the catheter may include advancing an obstructive matter moving device (e.g., an embolectomy device) from the catheter and using the obstructive matter moving device to move obstructive matter through the distal end opening and into the lumen of the catheter. One non-limiting example of the types of obstructive matter moving devices that may be used is a device having an expandable element that is expanded within the body lumen such that obstructive matter becomes entrained in or engaged by the expandable element in a manner that allows it to thereafter move some or all of the obstructive matter. Such an expandable element may then be retracted, along with obstructive matter that has become entrained in or engaged by the expandable member, through the distal end opening and into the lumen of the catheter. In some examples, the method may further include delivering a therapeutic substance. For example, in cases where the obstructive matter comprises thrombus, a thrombolytic agent or other substance that may dissolve some of a thrombus and/or deter adherence of the thrombus to a wall of the body lumen may be delivered. In some embodiments where an obstructive matter moving device is used, such obstructive matter moving device may be initially used to canalize or compress the obstructive matter in a manner that improves blood flow through or around the obstructive matter for a period of time and, thereafter, is used to move at least some of the obstructive matter through the distal opening and into the lumen of the catheter.

Still further in accordance with the present disclosure, a method for increasing flow of a body fluid (e.g., blood) through an obstructed body lumen is described. Such a method may include inserting a catheter that has a proximal portion, a distal portion, a lumen, and a distal end opening into a body of a subject. The catheter may be transitionable from a first configuration in which the distal portion has a first outer diameter that is smaller than an outer diameter of the proximal portion and a second configuration in which the distal portion is expanded to a second outer diameter that is larger than the first outer diameter and, in some embodiments, no larger than the outer diameter of the proximal portion. Additionally, the method may include positioning the catheter, while in the first configuration, such that the distal end opening is within a body lumen. Further, the method may include causing the catheter to transition from the first configuration to the second configuration, and using the catheter to deliver a treatment that restores or improving flow of a body fluid (e.g., blood) through an obstructed body lumen. In some embodiments, the treatment delivered may comprise the delivery of a therapeutic substance (e.g., a thrombolytic agent) of a type and in an amount that is effective to improve flow of body fluid through the body lumen. In some embodiments, the treatment delivered may comprise use of a device that canalizes or compresses obstructive matter in a manner that improves flow of body fluid through or around the obstructive matter.

In other embodiments, an expandable guide catheter may be used to perform therapy. The expandable guide catheter can include a side port located proximal to an expandable distal region of the catheter. The side port of the expandable guide catheter may communicate fluidly between an environment external to the catheter and an internal lumen of the catheter. The expandable guide catheter may include a translation dilator that includes at least one window that can be aligned with the side port on the exterior of the catheter to permit fluid communication between the external environment adjacent the catheter and the internal lumen of the catheter. The internal lumen may reside radially inside the translation dilator. The expandable guide catheter can further include a removable obturator or lead guidewire. The expandable guide catheter may serve as a temporary shunt for the vasculature or other body lumen.

In use, the therapeutic expandable guide catheter may be advanced toward and through an obstruction such as a clot or region of spasm within a vessel. The obstruction may be penetrated by the removable obturator or guidewire which may be followed by the radially collapsed distal end of the expandable guide catheter. The obturator may be removed once the obstruction is fully penetrated and the distal end of the expandable region is securely within the unobstructed vessel lumen distal (e.g., downstream) of the obstruction. The translation dilator may then be advanced distally to expand the distal, expandable region. Additionally, the window in the side wall of the translation dilator may be aligned with the port or window in the proximal portion of the expandable guide catheter. In other embodiments, the obturator can remain within the translation dilator while it is being advanced distally to expand the distal, radially expandable region. Blood flow through the vessel obstruction can be restored in this way since blood can flow into the window or port within the sidewall of the expandable guide catheter and flow out through the open distal end of the central lumen of the translation dilator. In other embodiments, blood flow can also be restored or improved in the reverse direction.

The present disclosure also generally relates to constructions for intravascular treatment devices useful for removing vascular occlusion material from a vascular occlusion or other tissue or material from a vascular lumen. The present disclosure more specifically relates to expandable intravascular occlusion material removal devices, as well as to methods of using those devices to treat eye diseases and conditions.

Vascular diseases, for example, may take the form of deposits, growths, or other tissue or material in a patient's vasculature which may restrict, in the case of a partial occlusion, or stop, in the case of a total occlusion, antegrade blood flow to a certain portion of the patient's body.

Further non-invasive, intravascular treatments may exist that are not only pharmaceutical, but also revascularize blood vessels or lumens by mechanical means. Examples of such intravascular therapies include balloon angioplasty, atherectomy, and vascular dilator(s), which physically revascularize a portion of a patient's vasculature.

Balloon angioplasty may include intravascular insertion of a balloon catheter into a patient through a relatively small puncture, which may be located proximate the groin, and intravascularly navigated by a treating physician to the occluded vascular site. The balloon catheter may include a balloon or dilating member which may be placed adjacent the vascular occlusion and then inflated. Intravascular inflation of the dilating member by sufficient pressures, on the order of 5 to 12 atmospheres or so, may cause the balloon to displace the occluding matter to revascularize the occluded lumen and thereby restore substantially normal blood flow through the revascularized portion of the vasculature. It is to be noted, however, that this procedure does not remove the occluding matter from the patient's vasculature, but rather, displaces it.

While balloon angioplasty is quite successful in substantially revascularizing many vascular lumens by reforming the occluding material, other occlusions may be difficult to treat with angioplasty. Specifically, some intravascular occlusions may be composed of an irregular, loose, or heavily calcified material which may extend relatively far along a vessel or may extend adjacent a side branching vessel, and thus are not prone or susceptible to angioplasty treatment. Even if angioplasty is successful in revascularizing the vessel and substantially restoring normal blood flow therethrough, there is a chance that the occlusion may recur. Recurrence of an occlusion may require repeated or alternative treatments given at the same intravascular site.

Accordingly, attempts have been made to develop other alternative mechanical methods of non-invasive or less invasive, intravascular treatment in an effort to provide another way of revascularizing an occluded vessel and of restoring blood flow through the relevant vasculature. These alternative treatments may have particular utility with certain vascular occlusions, or may provide added benefits to a patient when combined with balloon angioplasty and/or drug therapies.

One such alternative mechanical treatment method involves removal, not displacement, as is the case with balloon angioplasty, of the material occluding a vascular lumen. Such treatment devices, sometimes referred to as atherectomy devices, use a variety of means, such as lasers, rotating cutters (e.g., blades), or ablaters, for example, to remove the occluding material. The rotating cutters may be particularly useful in removing certain vascular occlusions. Since vascular occlusions may have different compositions and morphology or shape, a given removal or cutting element may not be suitable for removal of a certain occlusion. Alternatively, if a patient has multiple occlusions in his vasculature, a given removal element may be suitable for removing only one (or less than all) of the occlusions. Suitability of a particular cutting element may be determined by, for example, its size or shape. Thus, a treating physician may have to use a plurality of different treatment devices to provide the patient with complete treatment. This type of procedure can be quite expensive because multiple pieces of equipment may need to be used (such intravascular devices are not reusable because they are inserted directly into the blood stream), and may be tedious to perform because multiple pieces of equipment must be navigated through an often-tortuous vascular path to the treatment site.

With the following enabling description of the drawings, the apparatus should become evident to a person of ordinary skill in the art.

V. BRIEF DESCRIPTION OF THE FIGURES

FIG. 1A illustrates an exemplary catheter of the present disclosure including a balloon configured for placement in the OA;

FIG. 1B is a cross-sectional view of the catheter in FIG. 1A taken along line B-B of FIG. 1A;

Figures 10A, 10B, 10C:
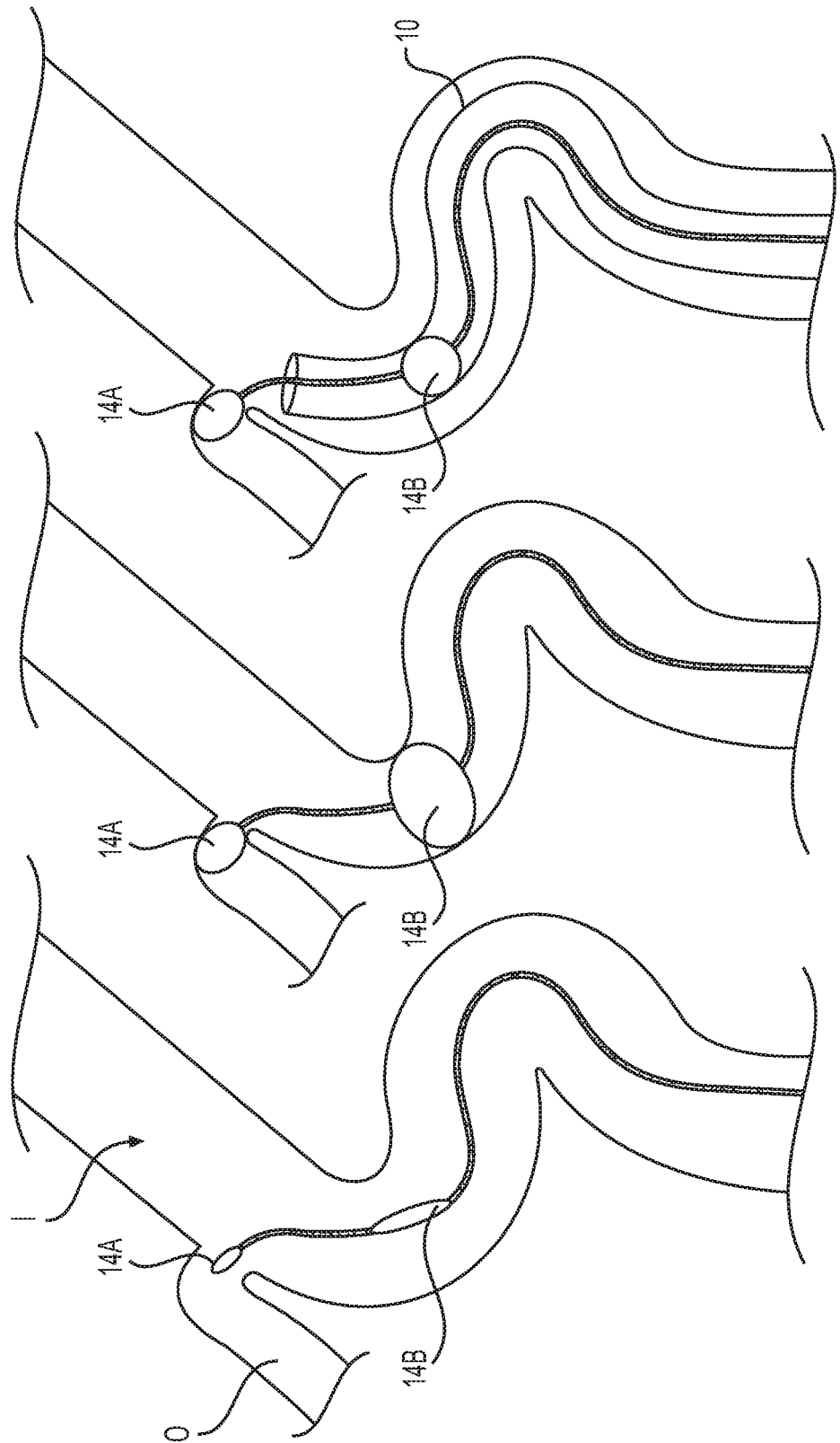
Figure 14C:
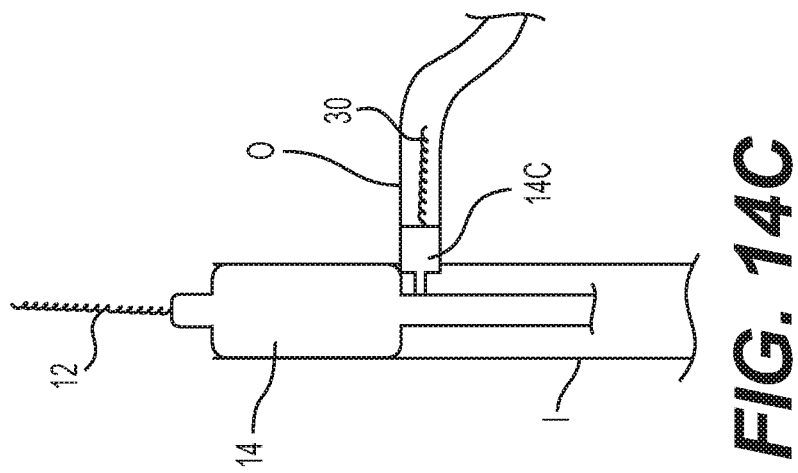
Figure 14B:
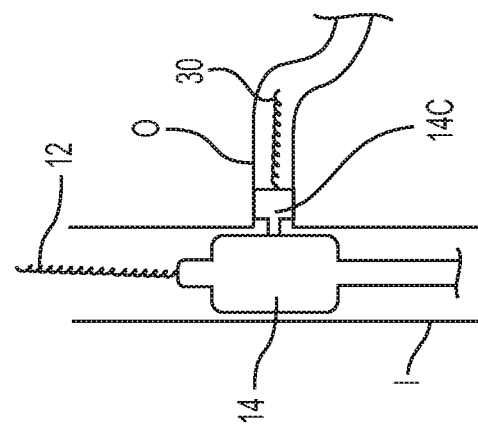
Figure 14A:
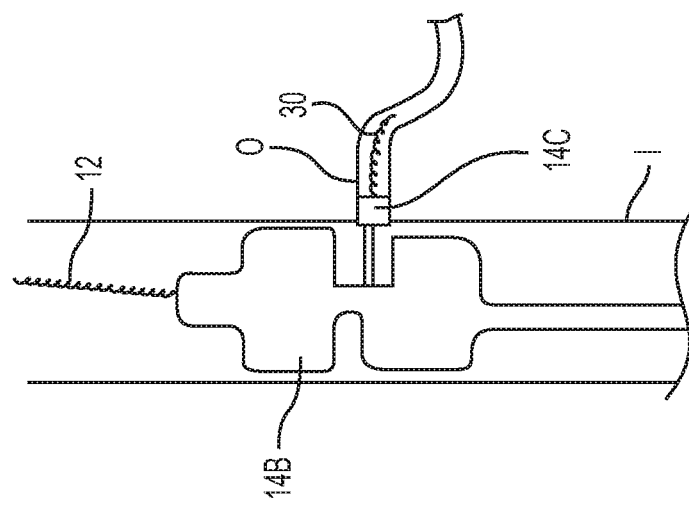
Figure 16A:
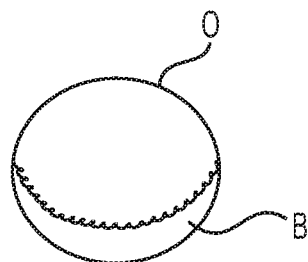
Figure 16B:
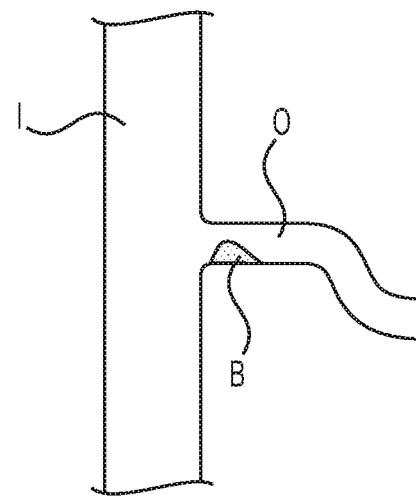
Figure 16C:
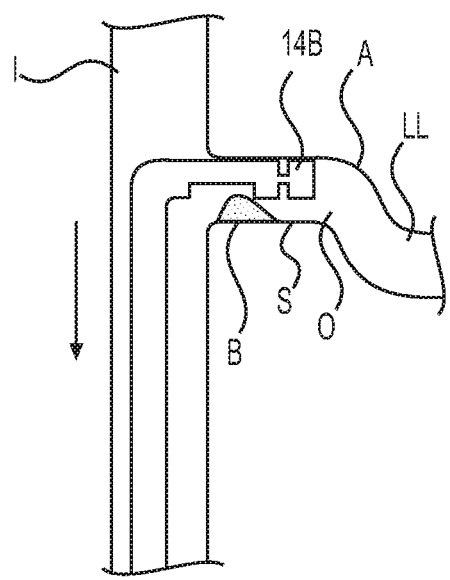
Figure 16D:
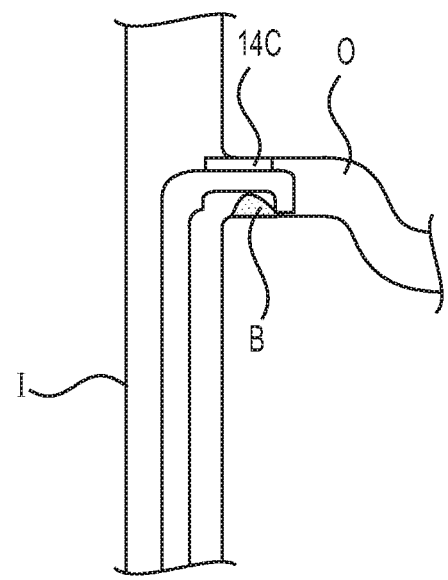
Figure 17:
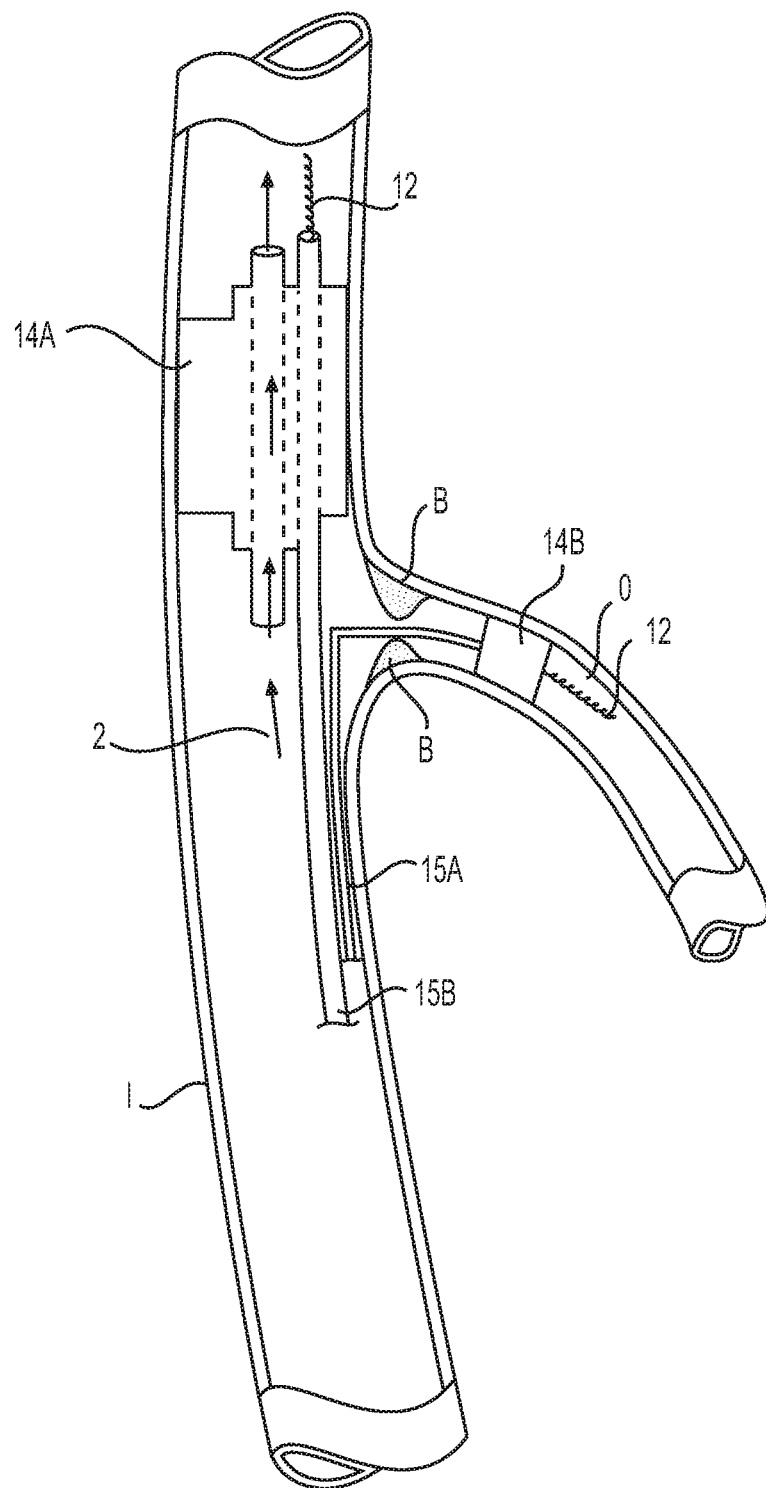
Figure 18:
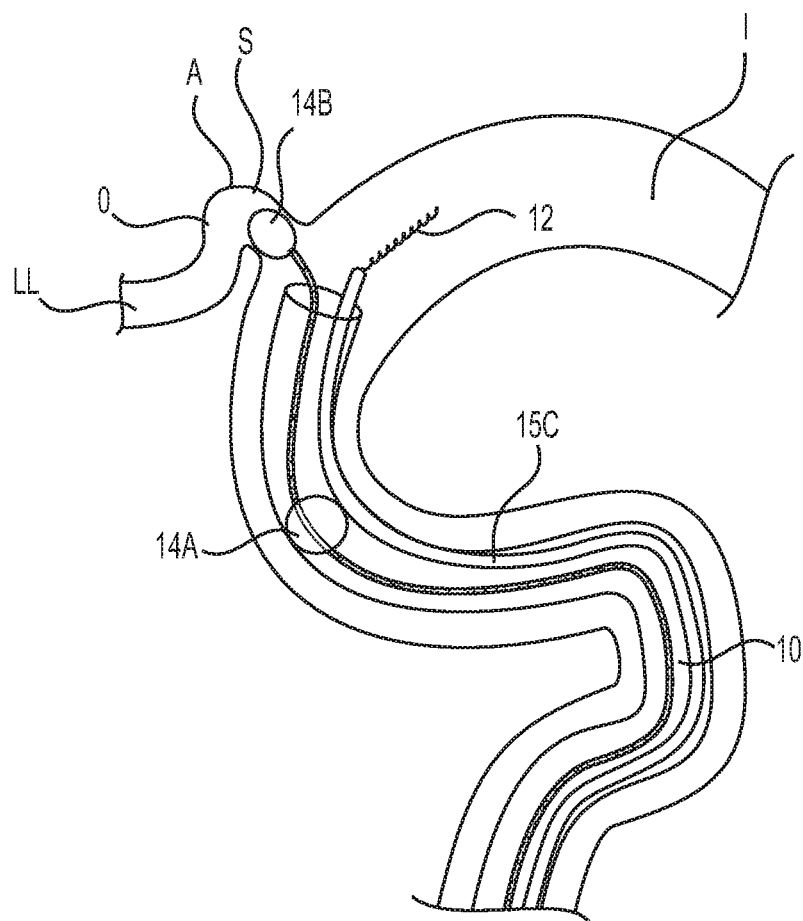
Figure 19:
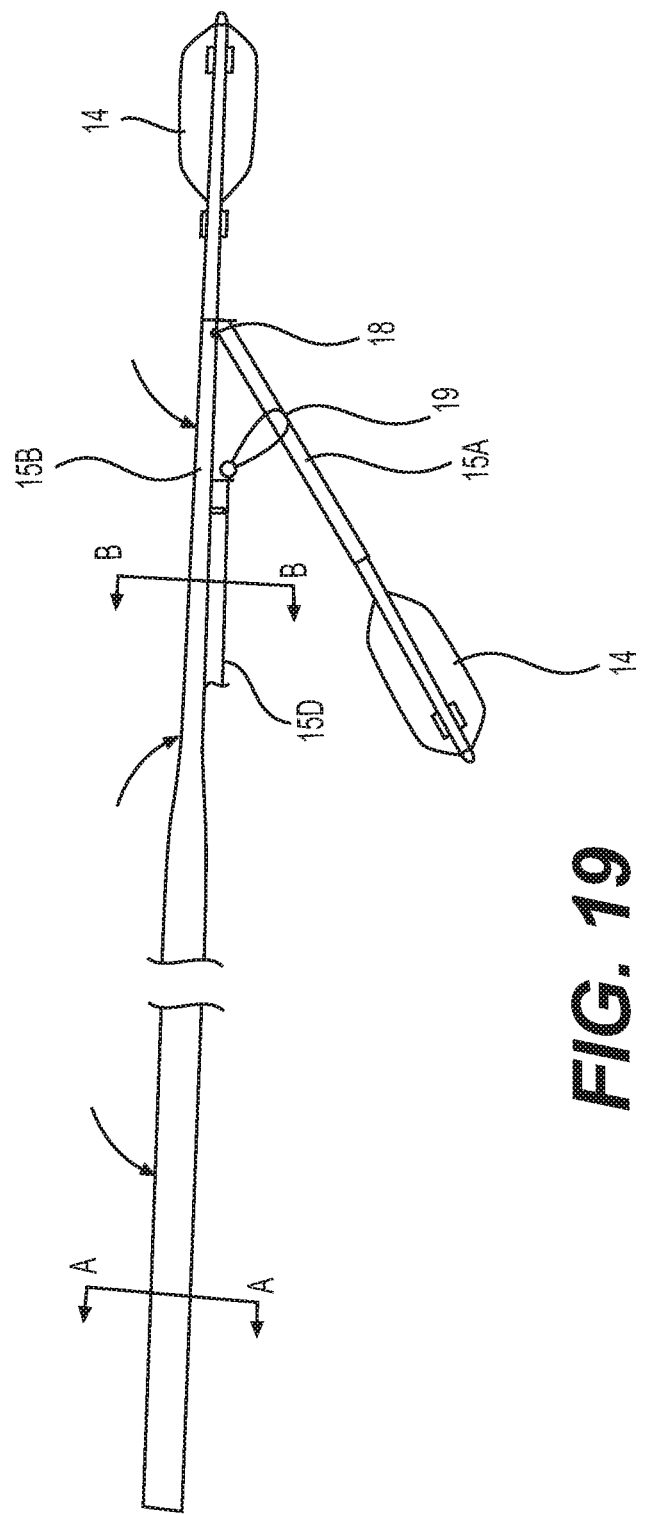
Figure 20:
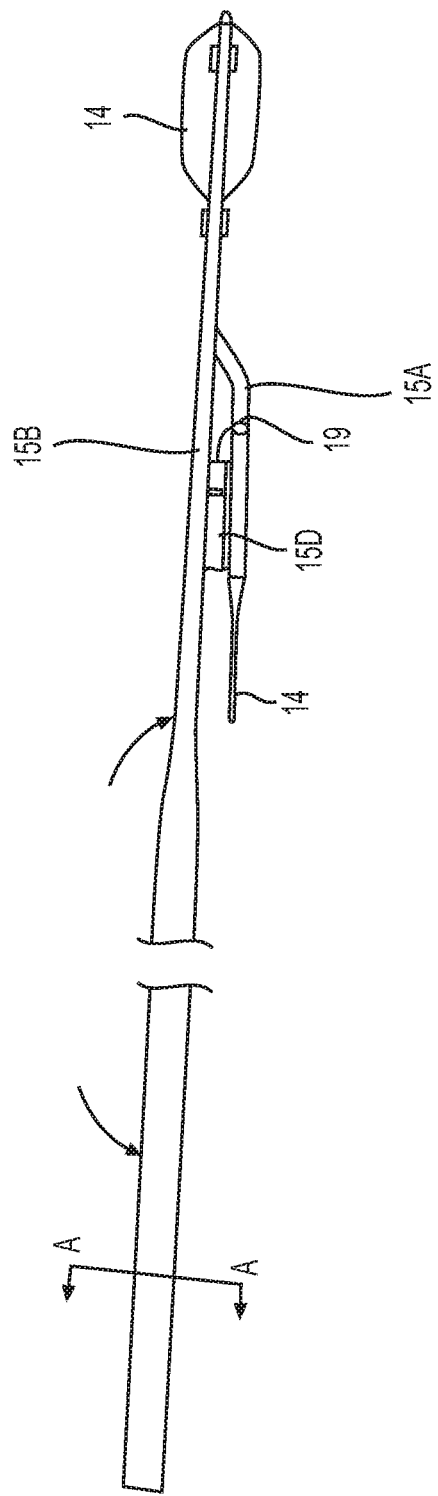
Figure 21:
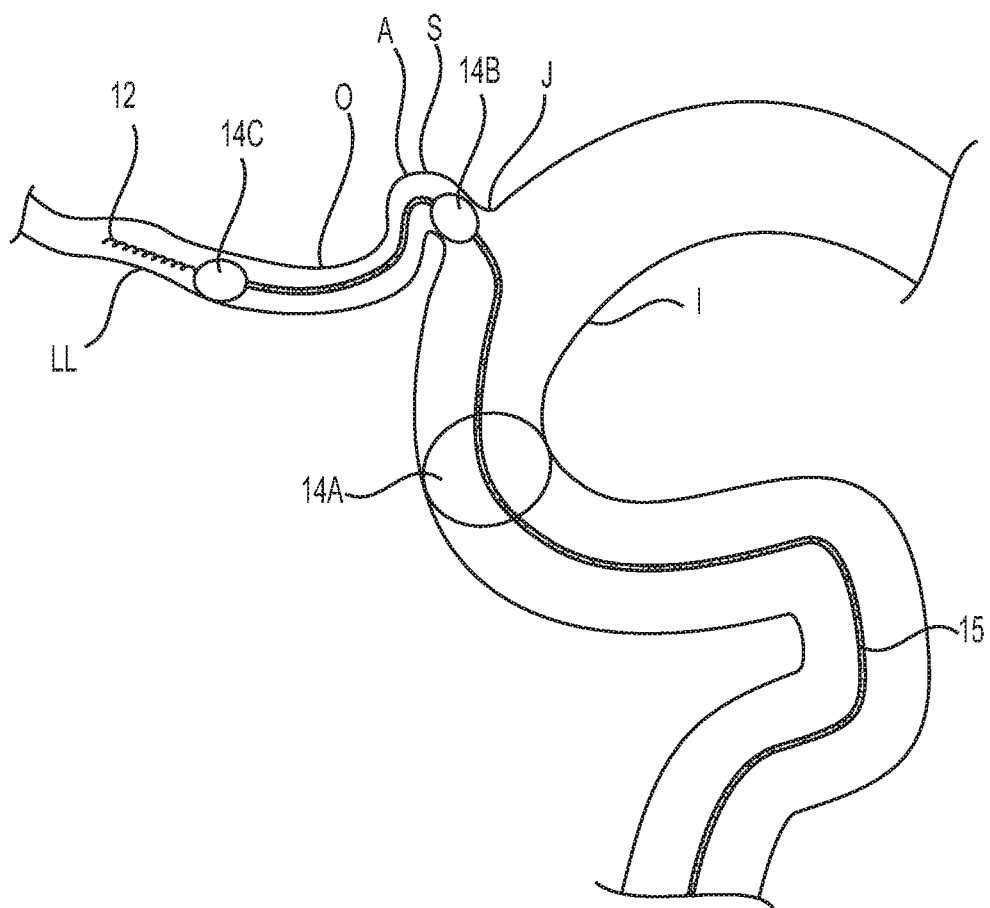
Figure 22:
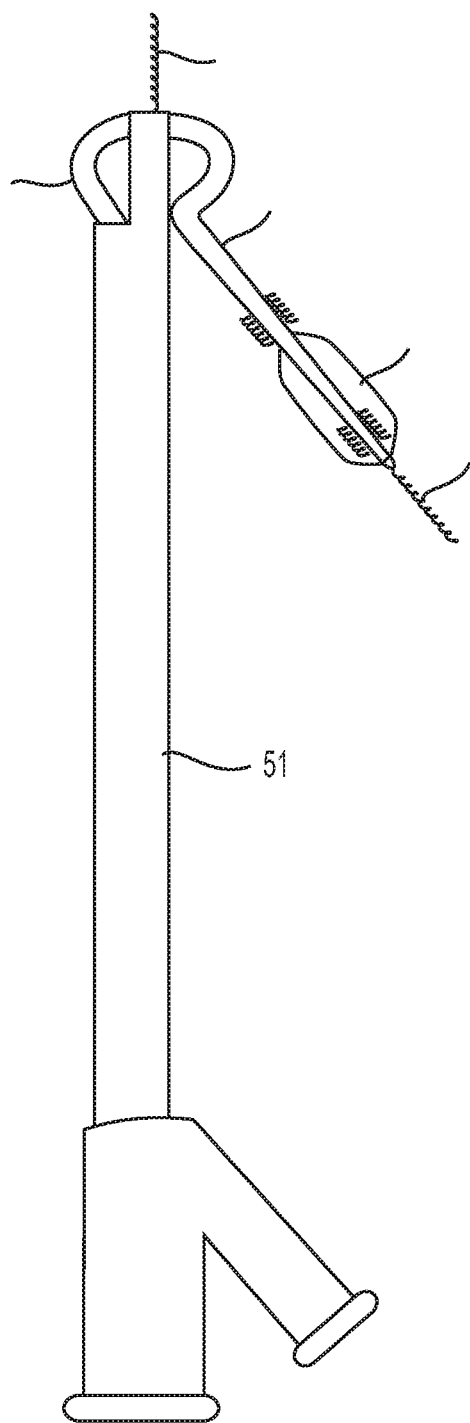
Figure 23:
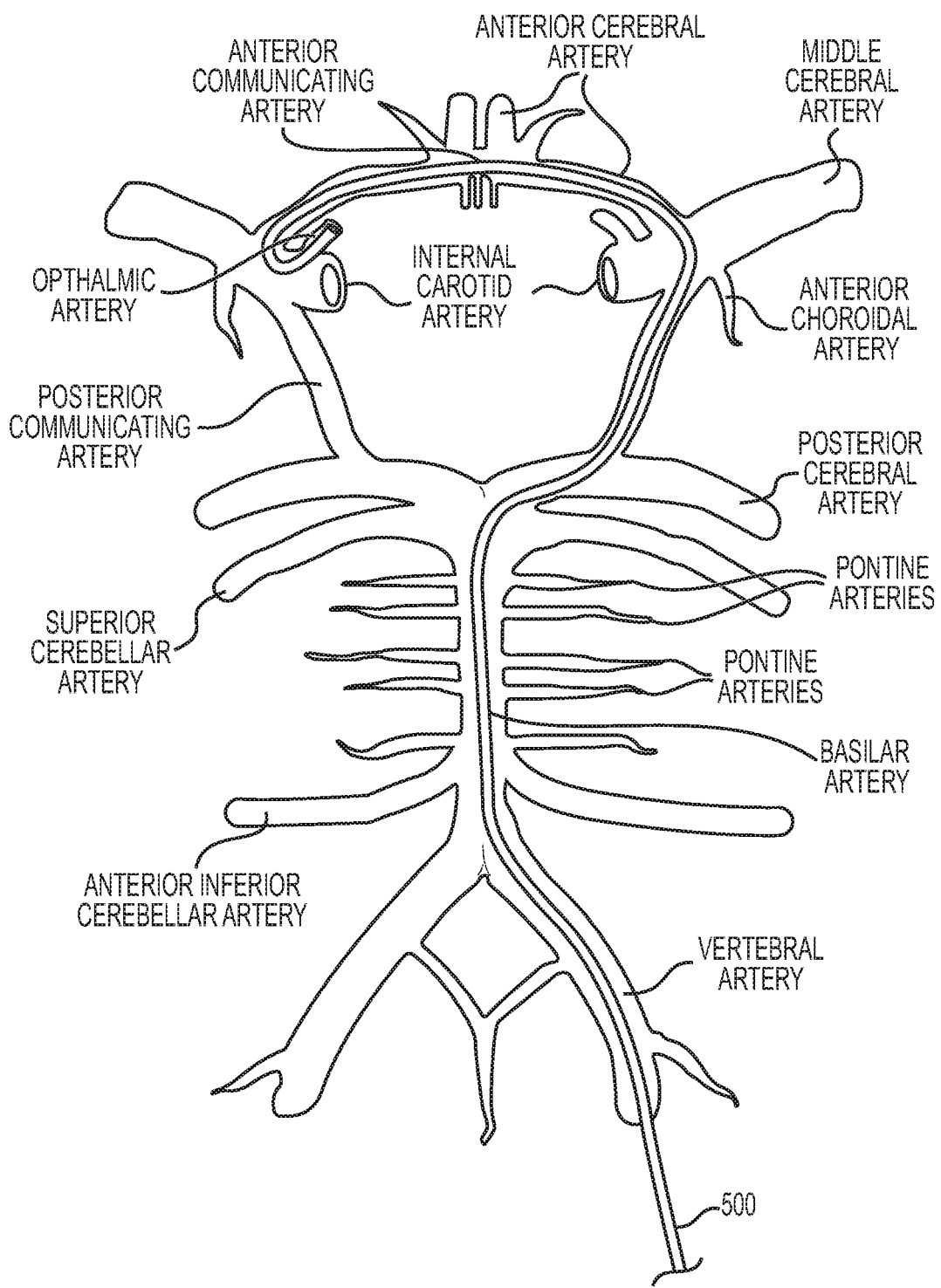

FIGS. 9 A-D illustrate a balloon device pre-shaped to conform to the ostium anatomy;

FIGS. 10 A-C illustrate a two-balloon medical device in which one balloon is configured for placement in the OA (e.g., a dilation balloon) and an anchoring or support balloon is configured for placement in the ICA, and a guiding catheter (FIG. 10C);

FIGS. 11 A-D show a close-up view of a balloon configured for use in the OA;

FIGS. 12 A-D show a variation of a balloon in which different attachment points to the guidewire allow the balloon to conform to the anatomy of the junction between the ICA and the OA;

FIGS. 13 A-C illustrate variations of a balloon and method in which the balloon intentionally slides out of the OA, thereby removing a blockage in the OA;

FIGS. 14 A-C illustrate alternative two-balloon configurations in which FIG. 14A shows a bifurcated first balloon and a second balloon shaped for placement in the OA;

FIGS. 15A and 15B illustrate alternative designs for a multiple lumen device;

FIGS. 16A and 16B illustrate a site-specific blockage in the OA;

FIGS. 16C and 16D illustrate alternative designs for removing a site-specific blockage in the OA;

FIG. 17 illustrates an embodiment of the present disclosure having a perfusion balloon;

FIG. 18 is an alternative embodiment of a perfusion system in which blood may flow through the catheter;

FIG. 19 illustrates an embodiment of a device in which a portion of the device is configured for the ophthalmic artery and can be mechanically extended or angled to conform to ICA/OA anatomy;

FIG. 20 illustrates the embodiment of FIG. 19 in a closed position;

FIG. 21 illustrates a three-balloon configuration having an anchor balloon and two ophthalmic artery balloons;

FIG. 22 illustrates a two-lumen configuration in which a balloon lumen is deployed in the ICA and enters the OA from the cranial or superior side; and FIG. 23 illustrates the delivery of a medical device toward the OA via a portion of the Circle of Willis.

VI. DETAILED DESCRIPTION

In at least certain embodiments, the present disclosure involves restoring or otherwise improving blood flow in arterial vasculature, including, for example, the OA, by delivering a balloon or expandable element to the OA, wherein said balloon is adapted and configured for placement in the OA, and wherein said balloon is used to restore blood flow in the OA. The expandable removal element may be movable between an expanded position and a contracted position and may be utilized in a single or multiple drive shaft configuration. Applicant notes that references throughout the disclosure to the OA are exemplary, and that in some embodiments, the devices, systems, and method described herein may be used to treat other arterial vasculature, such as vessels with small diameters and/or sharp-angled (e.g., tortuous) lumens.

The present disclosure also includes a medical device suitable for delivery and deployment within the ophthalmic artery. The device may be variously configured. The device may be a catheter comprising one or more lumens. The lumens may be used to house, deliver, and/or retrieve one or more elements suitable for restoring blood flow in the ophthalmic artery, typically by removing a blockage or the like. Exemplary elements include, but are not limited to, one or more guidewires, one or more balloons, one or more blockage capture and retrieval elements, one or more inflation elements (e.g., an inflation lumen), one or more filter elements, and/or one or more anchoring elements.

In some examples, the system for accessing the ophthalmic artery may comprise a catheter, typically a catheter suitable for use in angioplasty or atherectomy procedures. The catheter may also be a guide catheter.

In some examples, the medical device may include one or more lumens and elements as described above. In these arrangements, the medical device may not include a guide catheter.

The present disclosure also describes one or more devices comprising one or more balloons for performing the methods described above.

In some examples, the device may comprise a cutter and/or capture element for removing material from the ophthalmic artery. Some of these examples include a catheter and/or an aspiration lumen.

The present disclosure includes devices, methods, and systems for removing, or restoring flow through, blockage or occlusive material in a small diameter artery, such as the ophthalmic artery. The method may include the steps of providing a catheter having a proximal end and a distal end; at least one guidewire configured to extend from or pass through a distal tip of the catheter to a desired location; at least one lumen defining a channel within the catheter; and at least one balloon or expandable element configured for passing through a lumen of the catheter and/or comprising a distal portion of a guidewire. As is well known to those skilled in the art, placing the catheter, guidewires, and balloons in a particular portion of the anatomy typically requires the use of one of a variety of imaging techniques and devices, e.g., fluoroscopy.

Restoring and/or increasing blood flow is used herein to refer to any device, method, therapy, or combination that changes the blood flow to the eye. Examples of such include, but are not limited to increasing the blood flow anywhere in the vasculature leading to the eye or a portion of the eye; removing (e.g., atherectomy) or opening or displacing (e.g., angioplasty) an obstruction in the fluid flow path in the vasculature leading to the eye (e.g., from the ICA through the OA); delivering and deploying a stent in the fluid flow path in the vasculature leading to the eye; using atherectomy or similar devices to physically remove portions of any obstructions in the vasculature leading to the eye or portion of the eye; and localized drug and/or an oxygen device for increasing flow or amount of oxygen in one or more eye tissues. In some examples, a device or method of the present disclosure may be combined with a known or new drug or oxygen device in order to treat one or more eye diseases or conditions.

The present disclosure may also include restoring and/or increasing the amount of nutrients that are available to one or more parts of the eye or to the eye area, specifically by removing or partially opening a blockage in one or more of the arteries that supplies blood flow to the eye. In some examples, a blockage is removed or opened in the ICA, the OA, the ostium (as used herein, referring to the junction between the ICA and the OA), or combinations thereof. To or near the eye, as used herein, refers to the vasculature system that supplies blood to the various structures of the eye. As noted above, nutrients as used herein include, but are not limited to, oxygen, hemoglobin, complement, and glucose.

The present disclosure may also include methods, devices, and systems for removing or displacing a blockage in the ostium or a proximal segment (e.g., short limb) of the OA near the ICA. In such arrangements, removing or displacing the blockage comprises opening a channel or access through the ostium sufficient to provide a therapeutically beneficial result to the eye, the rear of the eye, or portions thereof. In some arrangements, removing a blockage involves atherectomy devices and methods. In some arrangements, opening or displacing a blockage involves angioplasty devices and methods. The present disclosure also includes restoring and/or improving blood flow anywhere in the vascular pathway to or within the eye.

Therapeutically beneficial result is used herein to refer to any perceived or actual benefit to the patient. Examples of beneficial results may include but are not limited to: treatment of an eye disease, condition, and/or symptom; restoring or increasing blood flow in any manner that treats an eye disease, condition, and/or symptom; and removing or partially removing a blockage in the blood flow path between the heart and the eye, in the OA or a portion thereof.

The present disclosure should not be limited solely to changing vascular flow in order to improve or restore the amount of nutrients that are delivered to the eye. For example, in some examples, the vascular flow may be unaffected for the most part, but the amount or concentration of nutrients may be increased, thereby increasing the amount of nutrients that may be delivered to the eye or associated with the eye. One skilled in the art may recognize, with the teaching of this disclosure, that there are other biological systems or capabilities that may be used to increase the amount of nutrients that are delivered to the eye.

In this and other aspects of the present disclosure, reducing or opening a blockage includes, but is not limited to, piercing or penetrating the blockage. In some examples, piercing and penetrating the blockage may refer to obtaining sufficient blood and/or fluid flow through or around a blocked vascular area sufficient to provide a therapeutically beneficial amount of oxygen (or other such nutrient) to the eye or a portion of the eye.

There is provided in accordance with one aspect of the present disclosure, a method for removing, opening, displacing, or restoring flow through thromboembolic material from a small diameter artery, such as the OA. Some methods involve using atherectomy devices and related procedures; other methods involve using angioplasty devices and related procedures. Still other methods include providing a catheter having a proximal end, a distal end, an expandable distal section having a distal port, an aspiration lumen communicating with the port, and an axially movable support. The method may include inserting the distal end of the catheter into an artery of a subject, and distally advancing the support to expand the distal section. Negative pressure is applied to the aspiration port, to draw the thromboembolic material into the distal section.

In accordance with another aspect of the present disclosure, there is provided an aspiration catheter. The catheter includes an elongate flexible tubular body, having a proximal end, a distal end, and an aspiration lumen extending therethrough. An aspiration lumen in a distal section of the flexible tubular body is movable between a first, reduced inside diameter for transluminal navigation and a second, enlarged inside diameter for aspirating material.

Alternatively, a catheter of the present disclosure may include one or more elements for physically capturing material and pulling it into the catheter and/or washing it away from the site of the occlusion.

In other embodiments, a microcatheter is disclosed, having an outside diameter of approximately 3-French or smaller, with the incorporation of an outer, diametrically expansile/contractile element near the distal region of the device. This expansile/contractile element coupled with the microcatheter system can serve a variety of therapeutic indications within the vasculature supplying blood flow or fluid flow to and from the eye. In some arrangements, the microcatheter can comprise a distention means for vascular anastomotic regions, flow restoration within an occluded vessel, foreign body retrieval, or an endovascular filter.

In an embodiment, the microcatheter can comprise means to deliver therapeutic devices and diagnostic agents (e.g., TPA) through one or more of the catheter's lumens or side holes, which further adds to this system's utility. The device's lumen, or lumens, could allow for aspiration and/or drainage.

Any of the devices, methods, embodiments, or variations of the present disclosure may be used with reverse flow or retrograde flow devices and methods. An exemplary description of reverse flow devices and methods includes, but is not limited to PCT/US17/21673 (filed 9 Mar. 2017) and U.S. Pat. No. 9,259,215, both incorporated by reference herein in their entireties.

A catheter or medical device of the present disclosure can be a tubular structure with distal and proximal ends and at least one lumen throughout its length or a portion of the catheter. The length of the catheter may be determined by its access point into the body, e.g., a transfemoral approach or a cervical approach. The length of the catheter for a transfemoral approach can be approximately 150 cm, and can range from about 100 cm to about 200 cm. The catheter can have an outer diameter with the diametrically expansile/contractile element contracted of no more than 1 mm (3 F). The length of the catheter for a cervical approach can be approximately 20 cm, and can range from about 10 cm to about 30 cm. The microcatheter advantageously comprises lateral flexibility, which can be constant or can include a plurality of increasingly flexible regions moving from the proximal to the distal end of the microcatheter. The microcatheter includes columnar strength sufficient to facilitate pushability/advanceability through the vasculature.

The outer diametrically expansile/contractile element, hereafter referred to as the expandable element, which can be generally affixed to the catheter shaft near the distal end of the microcatheter shaft, can be fabricated from a variety of metallic or polymeric materials, either porous, non-porous, or a combination of these materials. This expandable element can be located proximate the distal end of the micro-catheter. In other embodiments, the expandable element can be located flush against the distal end, or about 1-2 cm from the distal end to improve guidewire-aided navigation through tortuous vasculature. The design may be provided with the expandable element having a maximum, expanded outer diameter of about 0.5 mm to about 2.5 mm, or between about 1 mm and about 2 mm.

Methods of Use

Other aspects or embodiments of the present disclosure include methods of use. The catheter can be used to perform blockage retrieval, removal, displacement, or opening. In such an embodiment, the device may be first prepared by flushing or priming the lumen with saline. The catheter is then navigated to the site of the blockage. The catheter is advanced along a guidewire so that the expandable element is positioned within or through the blockage. The expandable element is then expanded, engaging the blockage. After engaging the blockage with the expandable element, the user can administer thrombolytic agents to further entwine or entrap the blockage. The blockage may then be removed from the vasculature via the catheter. Additionally, the user may elect to keep the expandable element expanded, and remove the catheter device from the vasculature. Lastly, the blockage removal could be aided by aspiration through the catheter side holes.

In other embodiments, the microcatheter can be used for the purposes of anastomosis distension or dilation, vascular foreign body retrieval, temporary dilatation and flow restoration through atheromatous plaque, and vascular embolic filtering. These goals can be addressed by inserting the proper therapeutic device, such as a dilatation balloon, grasper or basket device, high force mesh dilator, or distal protection filter, respectively, through the working lumen of the microcatheter.

In accordance with some embodiments of the present disclosure, the catheter and/or guidewire and/or balloon may be delivered or positioned at the proximal end of the OA by accessing the OA from a cranial or superior position. In some of these embodiments, the device may be passed through the Circle of Willis or a portion thereof, or one or more cranial arteries, and approach the OA from a cranial or superior direction in the ICA.

Balloons

In accordance with the present disclosure, the devices and methods described herein may include one or more elongation members, such as a balloon or inflatable member. These elongation members may be variously configured and may include multiple variations or alternatives. All of these configurations, variations, and alternatives are adapted and configured for delivery and/or placement in the OA, in the junction (e.g., ostium) between the ICA and the OA, and in the OA before the first bend (e.g., angle a) or turn (e.g., within the short limb of the OA).

An elongation member (as described further herein) or balloon of the present disclosure may be constructed of conventional materials; may be variously shaped (e.g., tiered, dog-bone shaped, oval, elliptical, or round); may comprise a drug or chemical (e.g., may be drug-eluting) having therapeutic benefit or purpose; and/or may be compliant, semi-compliant, or non-compliant throughout the balloon or a portion thereof.

Figure 1D:
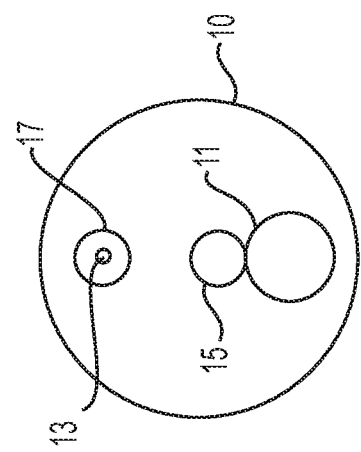
FIG. 1D is cross-sectional view of the catheter in FIG. 1A taken along line D-D of FIG. 1C.
Figure 1C:
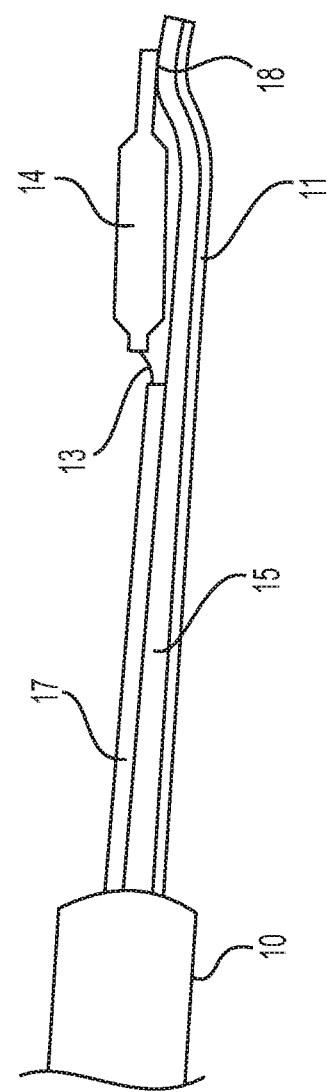
FIG. 1C is a side view of the catheter shown in FIG. 1A.

One embodiment of the elongation member is shown in FIGS. 1A and 1B. In this embodiment, a catheter/system 10 comprises a plurality of lumens including a first lumen 17 for housing, delivering, and deploying a balloon 14, a second lumen 11 for housing, delivering, and deploying a guidewire 12, and a third lumen 15 for delivering inflation fluid to the balloon 14 (e.g., via a distal end of balloon 14). The catheter also includes an elongation member 13 having balloon 14 coupled thereto. Elongation member 13 may extend to a proximal end of the catheter for manipulation (e.g., proximal retraction and/or distal advancement) by a medical professional. As shown in FIG. 1A, the catheter/system 10 is adapted and configured for delivery and placement in the junction J between the ICA I, and the OA O. That is, as shown, at least one or more of guidewire 12 and balloon 14 may be routed through junction (e.g., ostium) J and into a short limb S of OA O. Additionally, at least a portion of guidewire 12 may be advanced past angle A of OA O and into a long limb LL of OA O. FIGS. 1C and 1D illustrate additional views of the catheter of FIGS. 1A and 1B, having guidewire 12 removed therefrom. FIG. 1C also shows a place of fluid communication 18 between inflation lumen 15 and the distal end of the balloon 14. A side port in balloon 14 at its distal end may communicate with a side port in inflation lumen 15 at a place of fluid communication 18. In some embodiments, the inflation lumen 15 or inflated balloon 14 may sandwich or anchor the guidewire lumen 11 against the ostium O; in other embodiments the balloon 14 or inflation lumen 15 may sandwich or anchor the guidewire lumen 11 against the ostium O.

In this embodiment of the present disclosure, the configuration of the balloon 14, when inflated, sandwiches the guidewire 12, balloon 14, and/or lumen 11 in place, e.g., in the junction J between the ICA I and the OA O. For example, inflation of balloon 14 may result in sandwiching, pushing, or otherwise urging guidewire 12 into contact with a wall of the OA O. As such, the balloon 14 has sufficient compliance and/or flexibility to conform to the typical anatomy in this location. That is, the balloon 14 has sufficient compliance and/or flexibility so as to fill the short limb S of the OA O, thereby urging the guidewire 12 into contact with the wall of the OA O. The anatomy between the ICA I and the OA O includes the junction/ostium J, the short limb S, and angle A. The long limb is shown as LL. In this embodiment of the balloon 14, the balloon may be short, and does not watermelon seed out of place (e.g., slide away from its intended position in the junction between the ICA I and the OA O). When the balloon 14 is inflated, it has the ability to move with the anatomy. For example, inflation of balloon 14 may include performing an angioplasty on the OA and, since the OA expands with the inflated balloon 14, the OA is not dissected.

The elongation member 13 is preferably flexible (e.g., bendable), allowing the balloon 14 to move within the anatomy. Also, when the elongation member 13 is proximally retracted, a proximal end of the balloon 14 may be pulled in the proximal direction back into the catheter while a distal end of the balloon 14 is fixed relative to the guidewire lumen 11 in any appropriate manner (e.g., via adhesive, crimping, etc.), thereby preventing the balloon from buckling within the anatomy. That is, proximal retraction of elongation member 13 by a medical professional may likewise proximally retract a proximal end of balloon 14 relative to the distal end of balloon 14 which is fixed to inflation lumen 15. Accordingly, balloon 14 is stretched or elongated due to the relative movement between elongation member 13 and inflation lumen 15. Typically, the elongation member 13 may be made from an elastic polymer, spring, corrugated tube, nitinol, a telescoping tube or tubes, or a fixed wire. Balloon 14 may be extruded over the elongation member 13, thereby coupling the balloon 14 to the elongation member 13. In some arrangements, elongation member 13 includes a stretchable polymer. Alternatively, elongate member 13 may include a rigid cable or wire.

In some arrangements, the elongation member 13 may extend distally of, or may stop near, a proximal waist of balloon 14.

Further, the balloon 14 can be inflated from the distal end or from the proximal end of the balloon 14.

Figure 2:
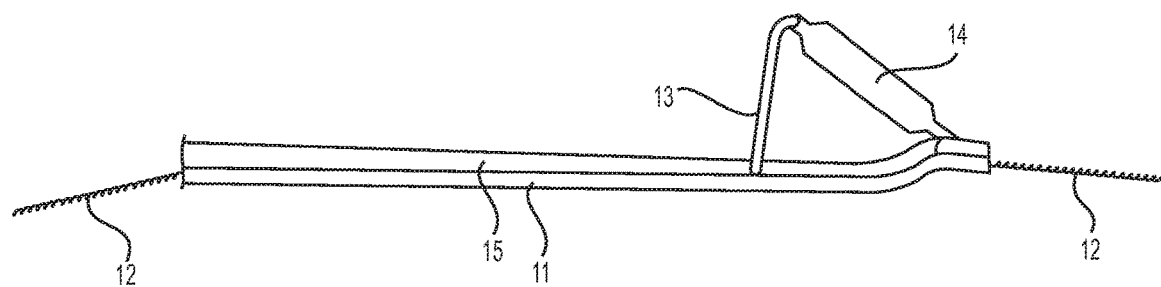
FIG. 2 illustrates a two-lumen catheter including a balloon attached to a band that stretches when the balloon is inflated and allows the balloon to conform to the anatomy between the ICA and the OA.
Figure 3:
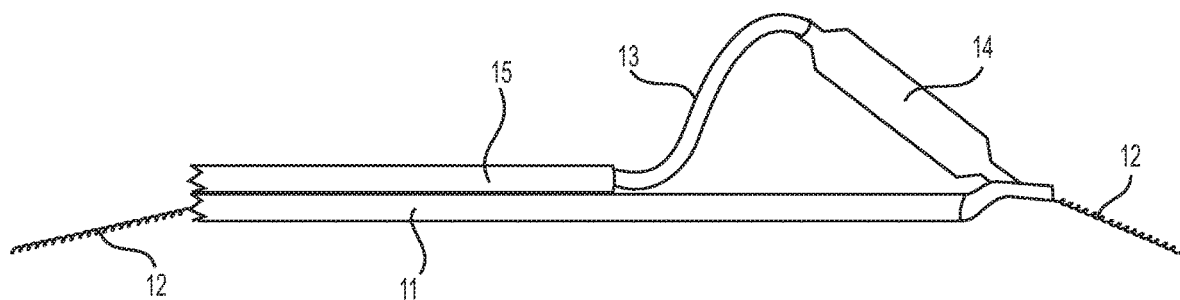
FIG. 3 illustrates a three-lumen device and an elongation member that allows the balloon to conform to the anatomy between the ICA and the OA.

Alternative designs are shown in FIGS. 2 and 3, which illustrate embodiments of the present disclosure in which the elongation member 13 is attached to a two- or three-lumen shaft, respectively. In this configuration, when the balloon 14 is inflated, an attachment (e.g., the elongation member 13) of the balloon 14 to the two- or three-lumen shaft at a proximal end of the balloon 14 stretches to match or conform to the anatomy In each of FIGS. 2 and 3, elongation element 13 may be arranged as an elastic band/tube having one end coupled to balloon 14 and an opposite end coupled to the catheter/system 10 (e.g., coupled to the inflation lumen 15). As balloon 14 is inflated, elongation member 13 may stretch. Additionally, balloon 14 may be inflated through a distal end of balloon 14, as shown in FIG. 2. In other arrangements, however, balloon 14 may be inflated through a proximal end of balloon 14, as shown in FIG. 3. In such an arrangement, inflation lumen 15 may communicate with elongation member 13 which may be in communication with a proximal end of balloon 14. In this example, elongation member 13 may be tubular so as to convey inflation fluid therethrough.

Figure 4:
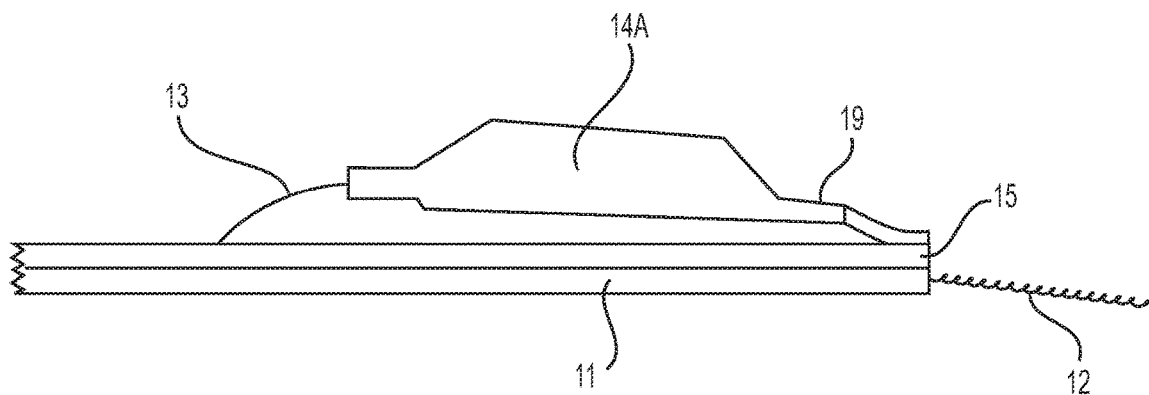
FIG. 4 illustrates a balloon which is offset or inflatable on one side so as to be asymmetrical.

FIG. 4 illustrates a configuration in which a balloon 14A is offset or asymmetrical. In this embodiment, balloon 14A is inflated through the distal end of balloon 14A via inflation lumen 15. For example, a distal waist 19 of balloon 14A may be fluidly coupled with inflation lumen 15, as will be described in further detail below.

Figure 5:
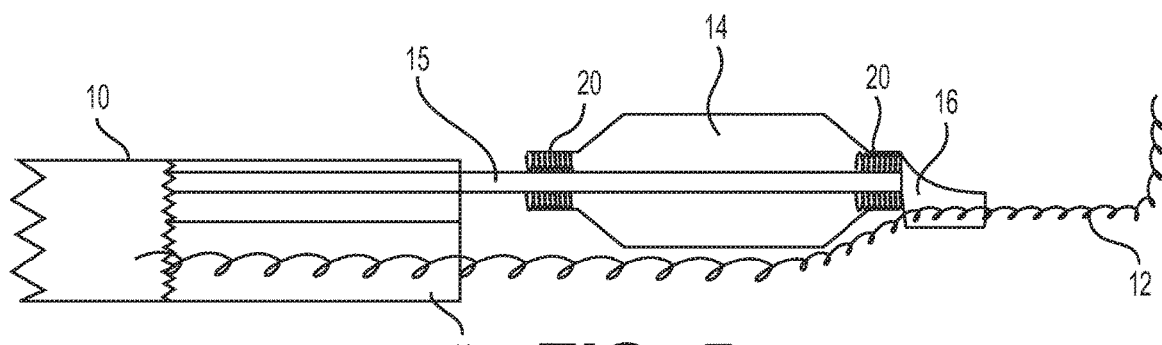
FIG. 5 illustrates a medical device in which a tip houses both a guidewire and a distal end of a balloon, and where the balloon lumen is flexible at both distal and proximal ends of the balloon.

FIG. 5 illustrates a configuration in which the inflation lumen 15 is flexible (e.g., axially moveable relative to) at least one end of the balloon 14. In the illustrated embodiment, the lumen 15 includes a flexible element 20 (e.g., a spring, coil, etc.) attached to the shaft of the lumen 15 on both the proximal end and the distal end of the balloon 14. A first (e.g., proximal) end of each flexible element 20 may be attached via any appropriate manner (e.g., adhesives, etc.) to inflation lumen 15 while a distal end of each flexible element 20 may be attached via any appropriate manner (e.g., adhesives, etc.) to balloon 14. In such a manner, flexible elements 20 may permit or enable relative movement between inflation lumen 15 and balloon 14. In some examples, each flexible element 20 may include a spring or coil that may extend and retract longitudinally. This embodiment shows a configuration for sandwiching or anchoring the guidewire 12 against a wall of an artery.

Arrangements of the present disclosure also may include a tip element 16 (FIG. 5) attached to the distal end of the balloon 14 (or the distal flexible element 20), and includes a lumen to further position the guidewire 12. Tip element 16 may be attached via any appropriate manner to one or more of a distal end of balloon 14, flexible element 20, and inflation lumen 15. Additionally, tip element 16 may include a passage or lumen through which guidewire 12 may be passed to direct advancement of balloon 14 relative to guidewire 12 or vice versa, or to maintain radial spacing between guidewire 12 and balloon 14.

Figure 7:
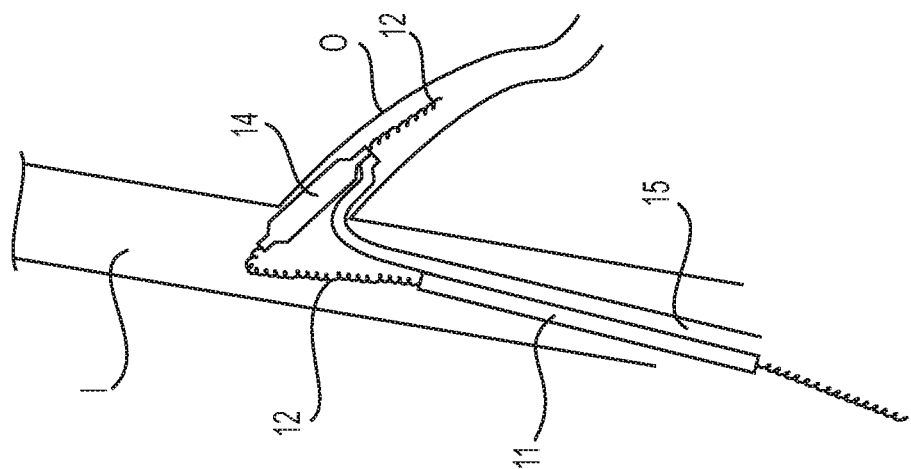
FIG. 7 illustrates a device according to the present disclosure in use within the ICA and the OA.
Figure 6:
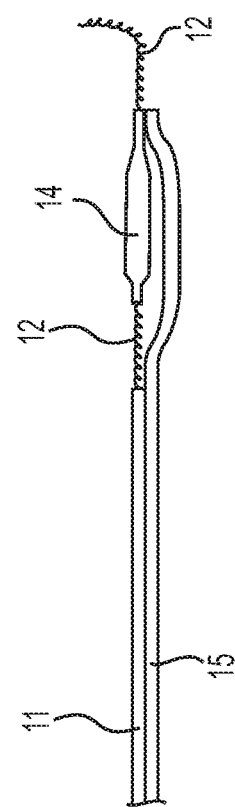
FIG. 6 illustrates a two-lumen catheter in which one lumen houses a balloon and a guidewire, and a second lumen is a balloon inflation lumen.

In another embodiment of the catheter/balloon configuration, illustrated in FIGS. 6 and 7, the guidewire lumen 11 includes a guidewire 12 that extends through a balloon 14. In the arrangement shown in FIGS. 6 and 7, guidewire 12 may act in the same manner as elongation member 13, described above. That is, in the arrangement of FIGS. 6 and 7, guidewire 12 may be used to extend or retract balloon 14 relative to inflation lumen 15. As such, guidewire 12 may be fixed relative to balloon 14 in any appropriate manner. Additionally, inflation lumen 15 is coupled to the distal end of the balloon 14. In such an arrangement, similar to that described above in FIG. 1C, a channel, lumen, or communication 18 may be provided between the distal end of balloon 14 and inflation lumen 15. In this embodiment, the balloon 14 and/or guidewire 12 allows the balloon 14 to conform to the anatomy, and the balloon 14 may be inflated from the distal end of the balloon 14. For example, during inflation, balloon 14 naturally wants to straighten. However, since the proximal end of balloon 14 is connected to flexible guidewire 12 and/or elongation member 13, the balloon is permitted to follow the trajectory of the OA (or ostium) rather than straighten out. That is, since the proximal end of balloon 14 is permitted to move relative to a distal end of balloon 14, balloon 14 may conform to the anatomy of the OA and/or ostium. In some embodiments, the guidewire 12 may be braided or coiled in a manner suitable for making the sharp turn or acute angle into the OA from the ICA.

Figure 8:
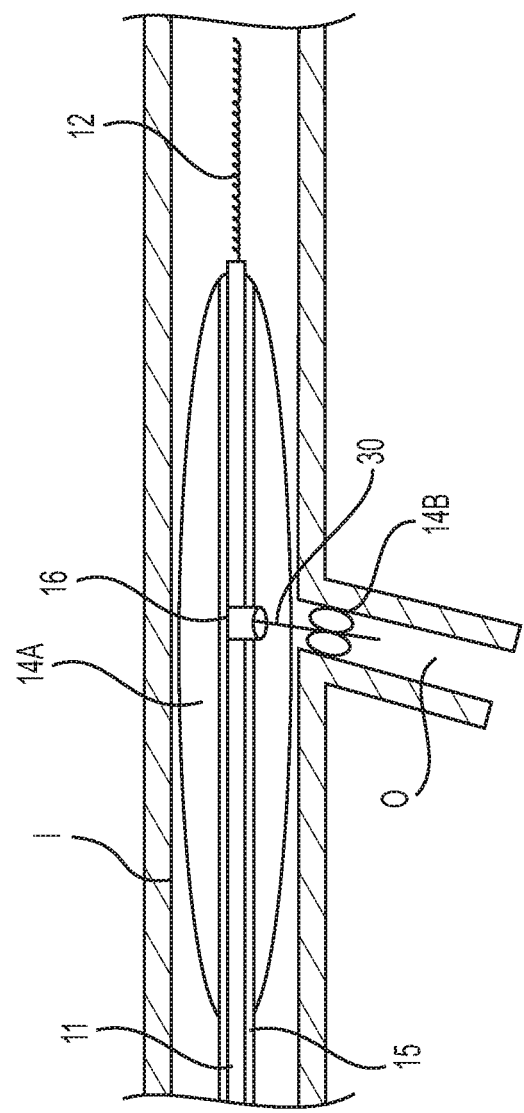
FIG. 8 illustrates a two-balloon medical device in which one balloon is adapted to conform to the ostium of the OA.

In another embodiment, the catheter comprises a plurality of lumens including a first lumen 11 for housing a conventional guidewire 12 and a second lumen 16 for housing a second guidewire 30 and a ball or balloon 14B, as shown in FIG. 8. Additionally, the arrangement of FIG. 8 would include an inflation lumen 15 in fluid communication with balloon 14A. Guidewire lumen 11 may extend the length of the catheter and through balloon 14A, the second lumen 16 may terminate at the first balloon 14A and extend through an opening in balloon 14A. For example, second lumen 16 may include a bend or turn that alters a direction of second lumen 16 so as to direct second guidewire 30 and balloon 14B in a direction angled with respect to guidewire lumen 11. In use, balloon 14A may be deployed in the ICA while second guidewire 30 and balloon 14B may extend through second lumen 16 to be positioned at the junction of the OA with the ICA. In this embodiment, the second balloon 14B is shaped (or pre-shaped) and configured to fit into the OA ostium (e.g., junction J). When positioned in the ostium, the balloon 14B may then be inflated to dilate the OA, to provide a stable base, and/or to prevent or reduce particle generation. As such, the side branch (e.g., second branch) guidewire 30 and balloon 14B may directly access the OA (e.g., for accessing and dilating the ostium junction J and/or short limb S). This embodiment also may include dual or multiple inflation lumens for the balloon(s).

The configuration shown in FIG. 8 also may include a perfusion feature or element, thereby allowing blood to flow through, past, or by the portion of the device in the ICA, as will be described in further detail below. The perfusion feature may be variously configured, including but not limited to a separate channel or lumen through the device; a through lumen on the side of balloon 14A; or grooves in the deployed balloon 14B. These embodiments of the present disclosure may further include a guidewire/balloon diverter configured to position the OA guidewire/balloon 14B in the OA. In the embodiments of the present disclosure that include a perfusion structure or element, an example of such a structure may be a side channel or pathway at or near the distal end of the balloon/lumen 14A positioned in the ICA. Other examples include, but are not limited to one or more channels in a central position of the balloon/lumen 14A; or near the proximal end of the balloon/lumen 14A.

In another embodiment, the catheter, balloon, and or guidewire may be pre-shaped (e.g., including a bent distal end angled to facilitate entry into the OA) to facilitate entry into the OA, as shown in FIG. 9A. The balloon 14 may be shaped to match or conform to the ostium O. For example, the OA may have a funnel or cone-shaped cross-sectional arrangement. That is, a diameter of the OA may vary along the length of the OA (e.g., may narrow such that a portion of the OA closer to the ostium may have a cross-sectional dimension larger than a portion of the OA farther away from the ostium). As such, balloon 14 may be likewise tapered such that the shape of the balloon 14 is complimentary to the shape of the OA and/or ostium. In FIG. 9B, the catheter positions the balloon 14 and guidewire 12 into the OA. In FIG. 9C, the guidewire 12 is removed or withdrawn, and in FIG. 9D, the balloon is inflated in the ostium. Once inflation is complete, the balloon 14 and guiding catheter 10 may be removed or withdrawn. In this embodiment, the balloon 14 may be designed to slip out of the anatomy or to be held in a static position during dilatation. For example, under pressure, the balloon 14 may displace from the OA short limb to the ICA (e.g., "watermelon seeding").

The balloon 14 and/or inflation lumen 15 may be pre-formed and shaped to conform to the anatomy at the junction J of the OA and the ICA, wherein the guiding or delivery catheter 10 straightens the balloon 14 and/or inflation lumen 15 during delivery and, when the catheter is withdrawn or the balloon 14 is pushed out of the catheter, its release thereby allows the balloon 14 and/or inflation lumen 15 to assume its pre-formed (angled) shape. That is, when positioned radially within guiding catheter 10, inflation lumen 15 and balloon 14 generally may extend along an axis extending through guiding catheter 10. Upon retraction of guiding catheter 10 relative to inflation lumen 15 and balloon 14, inflation lumen 15 and balloon 14 may deflect away from such an axis so as to form an acute bend arranged to facilitate entry into the OA. In some arrangements, one or both of inflation lumen 15 and balloon 14 may include a shape memory material (e.g., Nitinol) to facilitate bending or deflecting thereof.

In another embodiment, the catheter may include a dilatation balloon 14A and an anchor balloon 14B, positioned on one (e.g., the same) or more (e.g., different) guidewires. An illustration of this embodiment is shown in FIGS. 10A-10C in which inflation lumen 15 may include an extruded polymer tube or the like over a guidewire (e.g., a "balloon on a wire"). In this embodiment, the dilatation balloon 14A is shaped to conform to the OA (e.g., is sized such that upon expansion, dilatation balloon 14A contacts a wall of the OA), more specifically, the ostium junction J. In FIG. 10A, the dilatation balloon is positioned in the junction between the ICA and the OA and anchor balloon 14B remains uninflated. In FIG. 10B, the anchor balloon 14B is inflated, and then the dilatation balloon 14A is inflated. The anchor balloon 14B prevents the dilatation balloon from backing out from the ostium junction J into the ICA I. FIG. 10C shows an embodiment in which a balloon catheter is inside a guiding catheter 10, thereby anchoring balloon 14B to guide catheter 10 rather than a wall of the ICA.

Figure 11D:
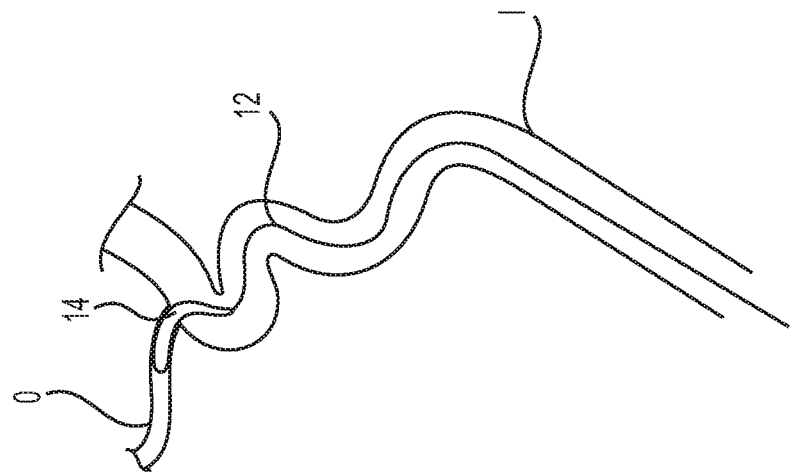
Figure 11A:
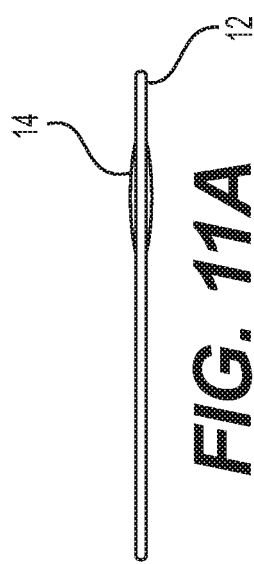
Figure 11B:
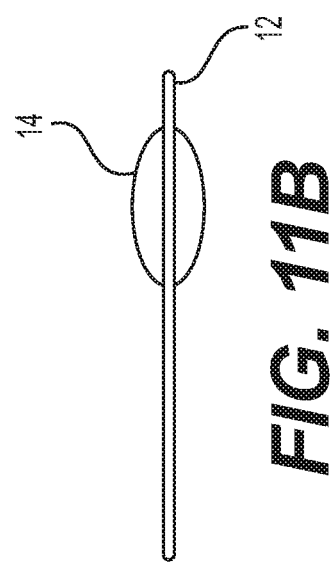
Figure 11C:
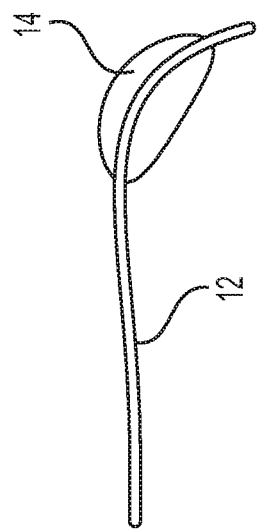

In another embodiment, the balloon and/or the guidewire may include a bias in one direction to conform the element(s) to the anatomy of the ICA and OA junction J. In preferred embodiments, the balloon and optionally the guidewire 12 are biased toward a deflected configuration. An example is shown in FIG. 11A-11C in which, as opposed to the arrangement of FIGS. 10A-10C where balloon 14 was coupled to inflation lumen, balloon 14 of FIGS. 11A-11C is coupled directly to guidewire 12. FIG. 11A shows an uninflated balloon 14 on a guidewire 12 designed to conform or fit into the ICA/OA ostium. During and after inflation, the bias in one direction allows the balloon 14 to conform to the angle of the junction J between the ICA and the OA (FIGS. 11B-11D) That is, the bias deflects one or more portions of balloon 14 and/or guidewire 12 at or along an angle (e.g., an acute angle) so as to enter the ostium junction J and/or OA O. The arrangement may be biased in any appropriate manner. For example, guidewire 12 may be pre-shaped to include a curve or bend. Additionally or alternatively, balloon 14 may be fabricated such that it is shorter on one side than the other, thus resulting in a biased or deflected arrangement upon inflation. In this embodiment, the bias is intended to prevent or reduce vessel straightening. That is, the short arm of the OA typically connects with the ICA at an angle. In particular, the connection may be curved. Biasing the balloon and/or guidewire may enable the balloon 14 and/or guidewire 12 to fit within this angled and curved structure without forcing the short limb of the OA to adjust the angle at which it extends from the ICA. In alternative embodiments, the bias may be in the guidewire alone, and may not include the balloon. Embodiments having a biased guidewire and/or balloon may further include a delivery or guiding catheter, or may not.

In another embodiment, the balloon is designed to fit or conform to the anatomy of the OA and/or the ostium by varying the point(s) of attachment to the catheter or guidewire. This fit or conformance in the ostium is intended to keep the distal portion of the balloon within the short arm of the OA such that when inflated, vessel straightening does not occur beyond the distal portion of the short limb of the OA. In a conventional arrangement, the balloon 14 is attached to the guidewire at both the distal and proximal ends of the balloon 14, as shown in FIG. 12A. In accordance with the present disclosure, the balloon 14 may be attached at the proximal end, but the distal attachment point may be closer to the center of the balloon 14 so as to cause portions of balloon 14 to overlap and/or invert on itself, thereby providing a discrete distal edge of the balloon 14 which substantially matches the distal anatomy of the short limb of the OA. As such, this distal edge of the balloon 14 will not extend past the distal most portion of the short limb. The distal attachment point may be varied along the body of the catheter or guidewire during device fabrication to provide adjustment of overall device flexibility. Two examples are shown in FIGS. 12B and 12C, in which the second attachment point is more proximal along the length of the balloon 14 than the distal end of balloon 14. In other words, the distal attachment between the balloon and the guidewire may be spaced proximally from a distal end of the balloon 14. In these embodiments, the distal attachment point allows a distal end of the balloon 14 to fold when the balloon is deflated so that the tip of the guidewire is more flexible. In a further embodiment, such attachment points may be designed to impart vessel straightening of the OA. FIG. 12 D shows a balloon 14 with an attachment point (e.g., a heat joint, adhesives, etc.) to a guidewire at the proximal end and a second attachment point at any point proximal of the distal end of balloon 14. As shown, the balloon 14 may fold of conform to the anatomy of the OA and/or the ostium. In some of these embodiments (not illustrated), a distal end of guidewire 12 may be flush with the distal end of the balloon. In other arrangements, a distal end of the guidewire 12 may extend distally of a distal end of the balloon.

The embodiments shown in FIGS. 12A-12D may be an over-the-wire configuration or a fixed wire configuration.

FIGS. 13 A-C show a guidewire 12 and distal balloon 14 configuration wherein the uninflated OA balloon 14 may be inserted into proximal end of the OA, e.g., at the ostium junction J. In this embodiment, the operation of which is described in more detail below, the compliant or semi-compliant balloon 14 may be placed in the OA, then inflated or partially inflated which forces the balloon out of the OA and into the ICA.

In another embodiment, a system comprises a first guidewire 12 configured for delivery and placement in the ICA adjacent the OA. As shown in FIG. 14A, this guidewire may include a first balloon, or in the illustrated embodiment, may include a bifurcated balloon 14B. The bifurcated balloon 14B may be configured so a first portion is adapted for placement in the ICA distal to the OA and a second portion is adapted for placement at the junction of the OA or just proximal of the junction of the OA. Bifurcated balloon 14B may have a narrowed or thinned portion in communication with the distal portion and the proximal portion which may enable additional flexibility to bifurcated balloon 14B The system further comprises a second guidewire 30 suitable for placement and entry into the OA O. The second guidewire 30 comprises a second balloon 14C configured and adapted for placement in the proximal end of the OA.

As shown in FIG. 14B, a single (e.g., non-bifurcated) balloon 14 may be used for the ICA balloon. In some embodiments, balloon 14 may include zones or sections of different compliancy. In some embodiments, balloon 14 may be compliant near the waist portion (e.g., FIG. 14A). Typically, a balloon in the ICA (or any structure not needing dilation) is compliant. A balloon (or balloon portion) 14C in the OA may be semi-compliant or non-compliant, and may or may not be inflated to a pre-determined and/or set pressure or size.

In another embodiment, shown in FIG. 14C, a first balloon 14 is not bifurcated, and is adapted for placement near but not over (e.g., distal of or downstream of) the entrance (e.g., the junction J or ostium) to the OA O, and the second guidewire 12 and second balloon 14C stem from the system or a second lumen of the system orthogonally or angled with respect to the first guidewire and first balloon.

In all of the embodiments shown in FIGS. 14A-C, the first balloon 14, 14B, helps stabilize the second balloon 14C when the second balloon 14C is inflated, keeping the second balloon 14C from watermelon seeding out of (or otherwise slipping out of) the OA upon inflation. In each of these embodiments, the balloons can be over-the-wire, rapid exchange, or fixed wire configurations.

In an embodiment, the system may include an inflation lumen 15 and a separate guidewire lumen 11. Two examples of such configurations are illustrated in FIGS. 15A and 15B. For example, FIG. 15A illustrates an inflation lumen coupled to a proximal end of a balloon, while FIG. 15B illustrates an inflation lumen extending through the balloon and coupled to a distal end thereof. Due to the inclusion of inflation lumen 15 extending through the balloon, the balloon of FIG. 15B may have a larger outer profile/dimension than the balloon of FIG. 15A In a method according to the present disclosure, the balloon may be intentionally underinflated. For example, a 2 mm diameter balloon (e.g., a balloon having a maximum inflated diameter of 2 mm) is inflated to produce only 1.25 or 1.50 mm diameter dilatation. The balloon is selected based on the desired dilatation outcome, e.g., larger than the diameter of the target anatomy. In these methods, the balloon, when inflated, intentionally slides out of the target anatomy (e.g., the OA). For example, a larger than required balloon may not be supported circumferentially in the ICA, and as such, the balloon may be free to watermelon seed out of the OA and into the ICA.

The balloon 14 may be partially inserted into the target anatomy (e.g., the OA). In some embodiments, only the distal ⅓ of the balloon 14 is inserted into the area of dilatation. The balloon 14 is then inflated at the lower end of its inflation capacity (e.g., about 6 to 8 ATMS). As the balloon 14 is inflated, the larger diametric area of the balloon (larger as compared to the ID of the target anatomy) will force the balloon 14 to slide out of the target anatomy and into the adjacent anatomy, e.g., slide from the ostium or OA and into the ICA in a retrograde manner or otherwise in a direction opposite that of antegrade blood flow.

In accordance with the present disclosure, the intentional use of the watermelon seed affect has a therapeutic effect: it opens or clears the ostium of any blockage or material covering the ostium.

The method used in this Example is illustrated in FIGS. 13 A-C. In FIG. 13A, a 2 mm diameter semi-compliant balloon (6 mm length) is inserted into the ostium of the OA, an area of the anatomy that is typically about 1 mm or less in diameter. In FIG. 13B, when the balloon is inflated to less than its nominal inflation pressure, the balloon is forced out of the OA into the ICA in a "watermelon seed" phenomenon. That is, if the balloon is inflated to a pressure less than that of the nominal pressure, the balloon may begin to exit the anatomy at low pressures. In FIG. 13C, the balloon completely exits the OA and enters the ICA, but in accordance with this method, partial dilatation of the ostium occurs, clearing any blockage in the ostium and the OA.

In the designs of the present disclosure, it may be desirable to coat the outside surface of the guidewire 12, the catheter body/system, and/or the balloon 14, 14A, 14B, 14C, and/or the inside surface of the wall defining a lumen of the catheter. Typically, these coatings are lubricious to minimize friction. A variety of coatings may be used, including but not limited to Parylene, Teflon, silicone rubber, polyimide-polytetrafluoroethylene composite materials, as well as other coatings known in the art.

Alternatively, the coating may be tacky, sticky, or include bumps or appendages specifically designed to hold or retain one or more elements in place or to otherwise inhibit movement of the one or more elements relative to the coating.

In another embodiment, a system may include one or more lumens and one or more guidewires. In some embodiments of the present disclosure the guidewire lumen may be sandwiched against the wall of an artery. In other embodiments of the present disclosure, the guidewire may be sandwiched against the wall of an artery.

In another embodiment, devices, systems, and methods may be used to address a site-specific blockage B in the OA, specifically in the ostium and/or the short limb S. For example, as opposed to other arrangements disclosed herein which may be used to treat a variety of anatomical locations (e.g., the OA, the ICA, the ostium, a carotid artery, or the like), further arrangements according to the present disclosure may be restricted for use in a particular anatomical location. A typical location of such blockages is shown in FIGS. 16A and 16B. FIG. 16C illustrates an embodiment in which a cutting catheter includes a cutter window and a cutting element adapted for communicating with the debris or blockage. Exemplary cutters include but are not limited to a pullback cutter, a push cutter, and a rotational cutter. A balloon 14B is shown in an exemplary position distal to the cutting window and the blockage B, and is configured and adapted for placement in the ostium or short limb S of the OA O.

An alternative configuration is shown in FIG. 16D, in which a balloon 14C is positioned adjacent the cutting element, and when inflated, the balloon anchors the cutter and pushes the cutter into the debris or blockage B.

In the embodiments shown is FIGS. 16C and 16D, the balloon(s) 14B, 14C block any debris from moving distally into the OA O, and aspiration may be used to remove the debris and/or occlusive material. Also, the side of the OA O in this location of the OA O may be used to place the cutter window within the blockage B or occlusive material. As noted above, the balloon 14B, 14C may be used to anchor the cutter, and it can also be used to push the cutter into the occlusive material or blockage B. For example, inflation of the balloon 14B, 14C may deflect or otherwise urge the cutter window towards the blockage B.

FIG. 17 illustrates an embodiment in which the system includes a perfusion feature, thereby allowing blood to flow past the ICA portion of the device (e.g., past balloon 14A inflated in ICA I). In the illustrated embodiment, blood flow is maintained (as illustrated by arrows 2) during the ICA balloon 14A inflation. In accordance with the present disclosure, any structure or configuration that allows blood to pass by the ICA portion of the system may be used, including but not limited to, a blood flow channel or lumen; grooves or channels in the ICA balloon 14A, one or more bypass channels or structures, and combinations thereof. In use, balloon 14A may be delivered over a first guidewire 12 arranged within inflation lumen 15B, while balloon 14B may be delivered over a second guidewire 12 arranged within inflation lumen 15A. Balloon 14A may have any appropriate shape including a channel to allow blood to perfuse therethrough.

This embodiment also shows two inflation lumens 15A and 15B. In this embodiment, inflation lumen 15B anchors or positions inflation lumen 15A in place, thereby anchoring the OA dilatation balloon 14B in the OA O.

Allowing blood to flow past the ICA portion of the device (e.g., past balloon 14A as shown by arrow 2) makes this embodiment particularly well suited for use with reverse or retrograde flow systems. For example, in arrangements in which the ICA is blocked thereby inducing reverse blood flow in the ICA, the perfusion lumen may be arranged to deliver blood in a retrograde or reverse direction (e.g., in the direction opposite the arrows 2).

FIG. 18 shows an alternative configuration that allows blood to flow past a portion of the device in the ICA (e.g., past balloon 14A). FIG. 18 illustrates an embodiment in which a catheter 10 includes at least one lumen 15C or channel within the catheter for allowing blood to pass through the ICA I (e.g., a perfusion lumen within which a guidewire 12 may extend). The illustrated embodiment also shows balloon 14A anchoring or positioning the lumen 15C in place. That is, inflation of balloon 14A in catheter 10 may deflect, urge, or otherwise push lumen 15C into engagement with a wall of catheter 10 to prevent movement of lumen 15C relative to catheter 10, which may prevent the balloon from watermelon seeding out the OA and into the ICA.

FIGS. 19 and 20 show an embodiment in which an OA portion of the device is configured sized, and/or shaped in a manner complimentary to the specific anatomy in the junction J between the ICA and the OA. In the illustrated embodiment, the OA portion of the device is hinged 18, articulatable, or movable in relation to an ICA portion of the device. The hinge 18 (or an articulation lumen) also anchors or supports the OA portion of the device in place in the OA.

The illustrated configuration may include an open and/or close mechanism or element for releasing the OA portion of the device (FIG. 19) or closing the OA portion of the device (FIG. 20). For example, a wire 19, loop, spring, or the like may be arranged about the OA portion device. For example, the device may include a lumen 15D though which wire 19 having a wire loop at a distal end thereof extends. The wire loop of wire 15 may surround the OA portion of the device and upon extension or loosening of the loop or wire 19, the OA portion of the device may deflect radially outwards away from the ICA portion of the device, as shown in FIG. 19. Upon retraction or tightening of the loop or wire 19, the OA portion of the device may deflect radially inwards toward the ICA portion of the device, as shown in FIG. 20.

In this embodiment, the device is adapted for delivery and removal from the ICA and OA. The device may be positioned in the ICA in its closed position (FIG. 20) above, superior, distal, or downstream to the OA. Next, the OA portion may be released, thereby facilitating entry into the OA (FIG. 19). Additionally, the device may be withdrawn from its position in the ICA by pulling the OA portion flush against the ICA portion of the device.

FIG. 21 shows an embodiment of the present disclosure comprising a balloon 14C configured and adapted for deployment or positioning in the long limb LL of the OA. In this embodiment, the device may include at least one balloon, and in the illustrated embodiment, three balloons. In the illustrated embodiment, balloon 14B anchors, stabilizes, or supports balloon 14C in place in the LL of the OA, and balloon 14A anchors, stabilizes, or supports balloon 14B in place in the short limb S or ostium junction J of the OA.

This configuration also illustrates the use of multiple balloons of different compliancy, e.g., balloon 14B is preferably compliant, non-compliant, or semi-compliant; balloon 14C is preferably compliant.

FIG. 22 shows an alternative configuration of a catheter having an OA lumen configured for deployment in the OA and adapted for the acute angle between the ICA and the OA. In the illustrated embodiment, the OA lumen and balloon may be deployed in the OA by first wrapping the OA portion around the ICA portion of the catheter and angling the OA portion down into the OA. This figure also illustrates another embodiment of the present disclosure, in which a lumen may be large enough to guide both the guidewire and the balloon. In the illustrated embodiment, guide catheter 51 is configured for positioning in the ICA. A balloon 14B and guidewire lumen 15A extend from a portion (e.g., a distal end) of the guide catheter 51, and loops around (e.g., behind) the guide catheter 51 and enters the OA from the superior or cranial side. In the illustrated embodiment, balloon 14B and guidewire lumen 15A are sized to position both a guidewire lumen and a balloon lumen, and configured to enter the OA. In some embodiments, balloon and guidewire lumens may be positioned in a tube or the like, which can in turn be heat shrunk to the desired size around the lumens. Additionally, FIG. 22 illustrates an arrangement in which balloon 14B includes a pair of attachment points for coupling balloon 14B to lumen 15A. As shown, the distal attachment point of the balloon 14B is provided proximally of the distal end of the balloon 14B.

The various embodiments of the present disclosure provide a number of constructions of expandable vascular material removal and/or opening devices, intravascular material removal and/or opening elements, and the like, which can be utilized to perform a plurality of different intravascular treatments, such as atherectomy, thrombectomy, angioplasty and the like. The embodiments of the present disclosure also provide a plurality of methods for using those devices and their associated vascular material removal or opening elements for performing intravascular treatments on a patient. It is to be fully recognized that the different teachings of the embodiments, examples, and arrangements disclosed herein can be employed separately or in any suitable combination to produce desired results. The embodiments provide, in the form of expandable intravascular removal or opening elements, ways of changing cutting or removing profiles, configurations or characteristics of a particular intravascular treatment device while only using a single removal or opening element. An inner hollow tube or sheath is located between an inner, proximal end of the housing. The inner sheath defines a lumen of dimensions sufficient for accepting a medical guidewire, made of stainless steel, nitinol, and the like, which can extend from the guidewire lumen within the inner sheath, and through an aperture in the proximal end of the housing to the exterior of the housing.

The hollow shaft also defines a guidewire lumen, thereby allowing for passage of the guidewire from the material removal element to the exterior of the housing. Thus, the removal device 10 is of an over-the-wire construction which can facilitate removing the device from, and replacing the device in the patient because the guidewire can remain within the patient. Comparatively, some prior art devices require removal of the guidewire along with the device, thereby necessitating additional intravascular navigation not only of the device, but also of the guidewire to replace the device adjacent the occlusion material to be removed. In addition, the presence of the guidewire facilitates intravascular navigation of the removal device, because the device can be delivered over the guidewire, which is an improvement over some expandable intravascular devices.

While an expandable intravascular removal or opening element is highly desirable for the reasons discussed earlier, it may be desirable to limit the maximum size of these intravascular elements. It may be desirable not to overexpand the expandable elements. While some means for positively limiting radial expansion of the expandable intravascular element have been detailed hereinabove, it may be desirable to provide additional safety mechanisms.

The removal or opening device may include a manifold assembly and a catheter assembly. Specifically, the manifold assembly includes a third port located distally of the port. The port may be connectable with a suitable source of fluid, not shown, but known in the art, for supplying the catheter assembly with fluid to dilate a dilating member for performing balloon angioplasty. The port may be located distally of a proximal end of the catheter assembly.

A dilating member, constructed substantially similarly to an angioplasty balloon, is located on the catheter assembly offset proximally of a distal end of the catheter assembly and the distal end of the drive shaft lumen. The inflation lumen extends from the port to a proximal end of the dilating member and conveys fluid from the fluid source, conventionally referred to as an inflation device, to and from the dilating member, thereby causing the dilating member to inflate and deflate. To facilitate intravascular location of the dilating member, a radiopaque marker band is provided on the outer surface of the drive shaft lumen, thereby rendering the intravascular portion of the dilating member radioscopically visible to a treating physician. Intravascular inflation of the dilating member provides added stability to the distal portion of the removal device during operation thereof, while also allowing the treating physician to occlude blood flow through the vascular lumen being treated and further allowing the physician to perform balloon angioplasty if desired. With the removal device it is possible for a treating physician to cut, remove, and/or angioplastically displace vascular occlusion material while only using a single piece of equipment.

Examples:

In a first cadaver lab experiment, a PTCA balloon was placed into the OA via the ICA in-situ, and inflated in the segment of the OA (e.g., the short limb S) proximal to the first sharp bend (e.g., angle A). In a second cadaver lab experiment, a PTCA balloon was placed and inflated in the target area ex-vivo, in the OA ostium. This experiment was repeated two times.

In both experiments, the balloon was successfully placed in the target area and dilated, without causing any apparent damage to the OA or the ostium.

The balloons used in the first experiment had a maximum inflated diameter of 0.8 mm at 16 ATMs. The working length was 3.5 mm. The balloon used in the second experiment had a maximum inflated diameter of 2.0 mm at 8 ATMs. The working length was 6.0 mm.

The in-situ experiment (e.g., first experiment) demonstrates that the balloon is capable of navigating the ICA anatomy, can be positioned in the short limb of the OA (before the first sharp bend in the OA), and inflated without causing any apparent damage to any of the vessels.

The ex vivo experiment (e.g., the second experiment) demonstrates that the balloon can be visualized in the correct location in the proximal end of the OA and can be oversized and inflated without causing damage to the OA or ostium.

These two experiments show that it would be possible to navigate and inflate a balloon catheter within the target anatomy of a living patient via an endovascular approach. These experiments also show that it is possible to precisely size a balloon catheter to the OA anatomy, or oversize a balloon catheter to the OA anatomy and dilate without causing damage to the anatomy.

In some aspects, accessing the OA or other anatomical locations may be difficult. For example, in guiding a medical device (e.g., a catheter, guidewire, etc.) to the OA, the medical device may be required to traverse tortuous anatomy requiring a number of sharp angled bends or direction changes. Indeed, to access the OA via the connected carotid artery via an inferior approach, the medical device may be required to bend at an acute angle. An alternative approach may be to access the OA from a cranial, upper, or superior position. That is, approaching the OA from a superior position may require advancing the medical device along a less tortuous path. As such, a medical device may more easily be introduced to the OA via the superior approach, which may result in reduced procedure time, reduced procedure cost, and reduced risk of damaging or rupturing an arterial structure or other tissues.

In accordance with exemplary methods of this disclosure, therefore, one or more devices may be delivered to, or introduced within, an identified anatomical location via the Circle of Willis, for example, by first traversing all or part of the Circle of Willis and approaching a target artery from a superior position. For example, in some arrangements, a medical device such as a catheter or guidewire 500 may be tracked (e.g., guided, steered, and/or passed) through either the left or right ICA, around a portion of the Circle of Willis (e.g., through the anterior communicating artery) into the other of the left or right ICA, and towards the OA. In such a manner, the guidewire wire 500 may approach the OA from an upper or superior direction so as to better align with the trajectory of the OA and reduce a tortuosity of the path through with the medical device may be passed.

For example, as shown in FIG. 23, guidewire 500 may be advanced through a vertebral artery, enter a posterior communicating artery of the Circle of Willis, through the right ICA, around a portion of the Circle of Willis superior to the ICA (e.g., the anterior communicating artery), into the left ICA, and into a target OA from a superior direction. The target OA may include a blockage (e.g., a complete or partial blockage) therein to be treated via any of the methods and devices described in this disclosure.

In additional arrangements, guidewire 500 may be tracked from an inferior direction (e.g., guided, steered, and/or passed) through a target ICA (e.g., the left ICA), around a portion of the Circle of Willis (e.g., via communicating arteries), and back into the target ICA (e.g., the left ICA) so as to approach the OA from an upper or superior direction.

In some arrangements, a percutaneous interventional device (e.g., a catheter and/or guidewire 500) may be advanced into the Circle of Willis from an inferior position and directed toward or into one or more arteries of the Circle of Willis. The one or more arteries may include the anterior cerebral arteries, the internal carotid arteries, branches of the internal carotid arteries, the vertebral arteries, the anterior communicating arteries, the posterior cerebral arteries, the basilar arteries, branches of the basilar arteries, and the posterior communicating arteries. Next, the percutaneous interventional device may be directed into the ICA and into a target OA from a superior position.

One skilled in the art will recognize that the present disclosure as described here may be reconfigured into different combinations, elements, and processes which are included within the scope of the present disclosure.

While the present disclosure has been described in some detail by way of illustration and example, it should be understood that the present disclosure is susceptible to various modifications and alternative forms, and is not restricted to the specific embodiments set forth in the Examples. It should be understood that these specific embodiments are not intended to limit the present disclosure but, on the contrary, the intention is to cover all modifications, equivalents, and alternatives falling within the spirit and scope of the present disclosure.

We claim:

1. A method for treating tissue of at least one of an internal carotid artery, an ophthalmic artery, or an ostium between the internal carotid artery and the ophthalmic artery of a subject, the method including:
   expanding a first expandable device of a first device in the internal carotid artery;
   delivering a second device into the ophthalmic artery via the first device and expanding a second expandable device of the second device in the ophthalmic artery; and
   adjusting an angle of the second expandable device relative to an axis of the first device from a first angle to a second angle different than the first angle, wherein, upon adjusting the angle of the second expandable device relative to the axis of the first device, the first expandable device is distal of the second expandable device.

2. The method of claim 1, wherein adjusting an angle of the second expandable device relative to the axis of the first device includes pivoting the second device relative to the first device via a hinge.

3. The method of claim 2, wherein pivoting the second device relative to the first device includes proximally tightening a loop around the second device.

4. The method of claim 2, wherein the hinge includes a spring.

5. The method of claim 1, wherein adjusting an angle of the second expandable device relative to the axis of the first device includes tightening a loop around the second device.

6. The method of claim 1, further including returning, after the adjusting an angle of the second expandable device relative to the axis of the first device, the second expandable device from the second angle to the first angle.

7. The method of claim 1, further including:
   removing the first device and the second device from the subject.

8. A method for treating tissue of at least one of an internal carotid artery, an ophthalmic artery, or an ostium between the internal carotid artery and the ophthalmic artery of a subject, the method including:
   delivering a first device having a first expandable device at a distal end thereof within the internal carotid artery, and expanding the first expandable device therein;
   delivering a second device having a second expandable device at a distal end thereof, within the ophthalmic artery, and expanding the second expandable device therein, wherein the second device is coupled to the first device via a hinge positioned upstream of the second expandable device; and
   manipulating a wire so as to adjust an angle of the second expandable device, relative to an axis of the first device, from a first angle to a second angle different than the first angle, wherein, upon adjusting the angle of the second expandable device relative to the axis of the first device, the first expandable device is distal of the second expandable device.

9. The method of claim 8, wherein the wire includes a distal loop, and wherein manipulating the wire includes at least one of tensioning or loosening the distal loop.

10. The method of claim 9, wherein the distal loop is looped around at least a portion of the second device.

11. The method of claim 10, wherein the at least the portion of the second device is upstream of the second expandable device.

12. The method of claim 9, wherein manipulating the wire so as to adjust the angle of the second expandable device, relative to the axis of the first device, from the first angle to the second angle, includes tensioning the distal loop.

13. The method of claim 12, further including loosening the distal loop, so as to adjust the angle of the second expandable device, relative to the axis of the first device, from the second angle to the first angle.

14. The method of claim 8, wherein the hinge includes a spring.

15. A method for treating tissue of at least one of an internal carotid artery, an ophthalmic artery, or an ostium between the internal carotid artery and the ophthalmic artery of a subject, the method including:
   delivering a device in a collapsed configuration to a location within the internal carotid artery, wherein, in the collapsed configuration, a first lumen of a first portion of the device is positioned alongside a second portion of the device;
   releasing the second portion of the device relative to the first portion of the device and inserting the second portion of the device within the ophthalmic artery; and
   manipulating a wire so as to adjust an angle of the second portion of the device, relative to an axis of the first portion of the device, from a first angle to a second angle different than the first angle, wherein, upon adjusting the angle of the second portion of the device relative to the axis of the first portion of the device, the first portion of the device is distal of the second portion of the device.

16. The method of claim 15, further including:
   expanding a first expandable device of the first portion of the device within the internal carotid artery.

17. The method of claim 16, further including:
   expanding a second expandable device of the second portion of the device within the ophthalmic artery.

18. The method of claim 15, wherein the wire includes a distal loop, and wherein manipulating the wire includes at least one of tensioning or loosening the distal loop.

19. The method of claim 18, wherein the distal loop is looped around the second portion of the device.

20. The method of claim 19, wherein the distal loop is positioned upstream of the second portion of the device.

* * * * *